United States Patent [19]
Livant

[11] Patent Number: 6,001,965
[45] Date of Patent: Dec. 14, 1999

[54] ANTICANCER COMPOUNDS AND METHODS

[75] Inventor: Donna L. Livant, Ann Arbor, Mich.

[73] Assignee: The Regents of the University of Michigan, Ann Arbor, Mich.

[21] Appl. No.: 08/915,189

[22] Filed: Aug. 20, 1997

Related U.S. Application Data

[63] Continuation-in-part of application No. 08/754,322, Nov. 21, 1996, Pat. No. 5,840,514.

[51] Int. Cl.$^6$ .......................... A61K 38/00; A61K 38/08
[52] U.S. Cl. ............................. 530/330; 514/17; 930/21
[58] Field of Search ........................ 514/2, 17; 530/330

[56] References Cited

U.S. PATENT DOCUMENTS

| | | | |
|---|---|---|---|
| 4,016,043 | 4/1977 | Schuurs et al. | 195/103.5 R |
| 4,018,653 | 4/1977 | Mennen et al. | 195/127 |
| 4,424,279 | 1/1984 | Bohn et al. | 436/534 |
| 5,051,448 | 9/1991 | Shashoua | 514/547 |
| 5,136,023 | 8/1992 | Hashino et al. | 530/350 |
| 5,169,862 | 12/1992 | Burke, Jr. et al. | 514/450 |
| 5,192,746 | 3/1993 | Lobl et al. | 514/11 |
| 5,264,358 | 11/1993 | Doersen et al. | 435/240.2 |
| 5,436,221 | 7/1995 | Kitaguchi et al. | 514/12 |
| 5,492,890 | 2/1996 | Ginsburg et al. | 514/12 |
| 5,523,209 | 6/1996 | Ginsberg et al. | 435/7.2 |
| 5,539,085 | 7/1996 | Bischoff et al. | 530/350 |
| 5,548,062 | 8/1996 | Isoai et al. | 530/326 |
| 5,559,103 | 9/1996 | Gaeta et al. | 514/54 |
| 5,576,423 | 11/1996 | Aversa et al. | 530/388.75 |

FOREIGN PATENT DOCUMENTS

| | | |
|---|---|---|
| 9524471 | 9/1995 | WIPO . |
| 9612823 | 5/1996 | WIPO . |

OTHER PUBLICATIONS

P. Calabresi and B.A. Chabner, "Antineoplastic Agents," In: *Goodman and Gilman The Pharmacological Basis of Therapeutics* (Pergamon Press, 8th Edition) (pp. 1209–1216).

J.H. Gerlach et al., "Multidrug Resistance," *Cancer Surveys*, 5:25–46 (1986).

J.H. Goldie and Andrew J. Coldman, "The Genetic Origin of Drug Resitance in Neoplasms: Implications for Systemic Therapy," *Cancer Research*, 44:3643–3653 (1984).

D. Livant et al., "Invasion of Selectively Permeable Sea Urchin Embryo Basement Membranes by Metastatic Tumor Cells, But Not By Their Normal Counterparts," *Cancer Research* 55:5085 (1995).

Bresalier et al., "The Laminin 1 Chain Ile–Lys–Val–Ala–Val (IKVAV)–Containing Peptide Promotes Liver Colonization by Human Colon Cancer Cells," *Cancer Research* 55:2476 (1995).

Eldred et al., "Orally Active Non–Peptide Fibrinogen Receptor (GpIIb/IIIa) Antagonists: Identification of 4–[4–[4–(Aminoiminomethyl) phenyl]–1–piperazinyl]–1–piperidineacetic Acid as a Long–Acting, Broad–Spectrum Antithrombotic Agent," *J. Med. Chem.*, 37:3882 (1994).

Ku et al., "Potent Non–Peptide Fibrinogen Receptor Antagonists Which Present An Alternative Pharmacophore," *J. Med. Chem.*, 38:9 (1995).

W.R. Pearson and D.J. Lipman, "Improved Tools For Biological Sequence Comparison," *Proc. Natl. Acad. Sci.* (USA), 85:2444–2448 (1988).

D.J. Lipman and W.R. Pearson, "Rapid and Sensitive Protein Similarity Searches," *Science*, 227:1435–1441 (1985).

Douillard and Hoffman, "Basic Facts about Lymphocytes Hybridomas," *Compendium of Immunology* vol. II, ed. by Schwartz (1981).

G. Kohler and C. Milstein, "Continuous Cultures of Fused Cells Secreting Antibody of Predefined Specificity," *Nature*, 256:495–497 (1975).

G. Kohler and C. Milstein, "Derivation of Specific Antibody–Producing Tissue Culture and Tumor Lines By Cell Fusion," *European Journal of Immunology*, 6:511–519 (1976).

C.L. Reading, "Theory and Methods For Immunization in Culture and Monoclonal Antibody Production," *Journal of Immunological Methods*, 53:261–291 (1982).

Stone, K. R. et al., "Isolation of a Human Prostate Carcinoma Cell Line (DU 145)," *Int. J. Cancer*,21:274–281 (1978).

T. K. Gartner et al., "The Tetrapeptide Analogue of the Cell Attachement Site of Fibronectin Inhibitis Platelet Aggregation and Fibrinogen Binding to Activated Platelets," *The Journal of Biological Chemistry*, 260:11891–11894.

N.S. Nicholson et al., "In Vitro and In Vivo Effects of a Peptide Mimetic (SC–47643) of RGD As An Antiplatelet and Antithrombotic Agent," *Thrombosis Research*, 62:567–578 (1995).

M. Nomizu et al., "Multimeric Forms of Tyr–Ile–Gly–Ser–Arg (YIGSR) Peptide Enhance the Inhibition of Tumor Growth and Metastasis," *Cancer Research*, 53:3459–3461 (1993.

I. Saiki et al., "Inhibition of the Metastasis of Murine Malignant Melanoma By Synthetic Polymeric Peptides Containing Core Sequences of Cell–Adhesive Molecules," *Cancer Research*, 49:3815–3822 (1989).

R.H. Wenger et al. "Cloning of cDNA Coding For Connective Tissue Activating Peptide III From a Human Platelet–Derived AgtII Expression Library," *Blood*, 73(6):1498–1503.

(List continued on next page.)

*Primary Examiner*—Michael P. Woodward
*Assistant Examiner*—Michael Borin
*Attorney, Agent, or Firm*—Medlen & Carroll, LLP

[57] ABSTRACT

The testing of tumor cells, including human tumors capable of metastases, in assays employing fibronectin-depleted substrates is described. Ex vivo induction of cells, including biopsied human cells, is performed with invasion-inducing agents. Additionally, anti-cancer chemotherapeutics are described. Specifically, chemotherapeutic agents which have anti-metastatic and anti-growth properties are described.

5 Claims, 15 Drawing Sheets

OTHER PUBLICATIONS

Aota, S. et al., "The short Amino Acid Sequence Pro–His–Ser–Arg–Asn in Human Fibronection Enhances Cell-adhesive Function," *J. of Biol. Chemistry*, vol. 269,40:24756–24761 (1994).

Kumar, S. et al., "Childhood kidney tumours: in vitro studies and natural history," *Virchows Arch,* 405:95–111 (1984).

Atlas of Protein Sequence and Structure. National Biomedical Research Foundation, Washington, D.C., Jan. 1972, p. 96.

Song et al. J. Exp. Med.180(5), 1763–74, May 1994.

Hershey H. et al. Nucleic Acids Res., 13(23), 8543–59, Nov. 1985.

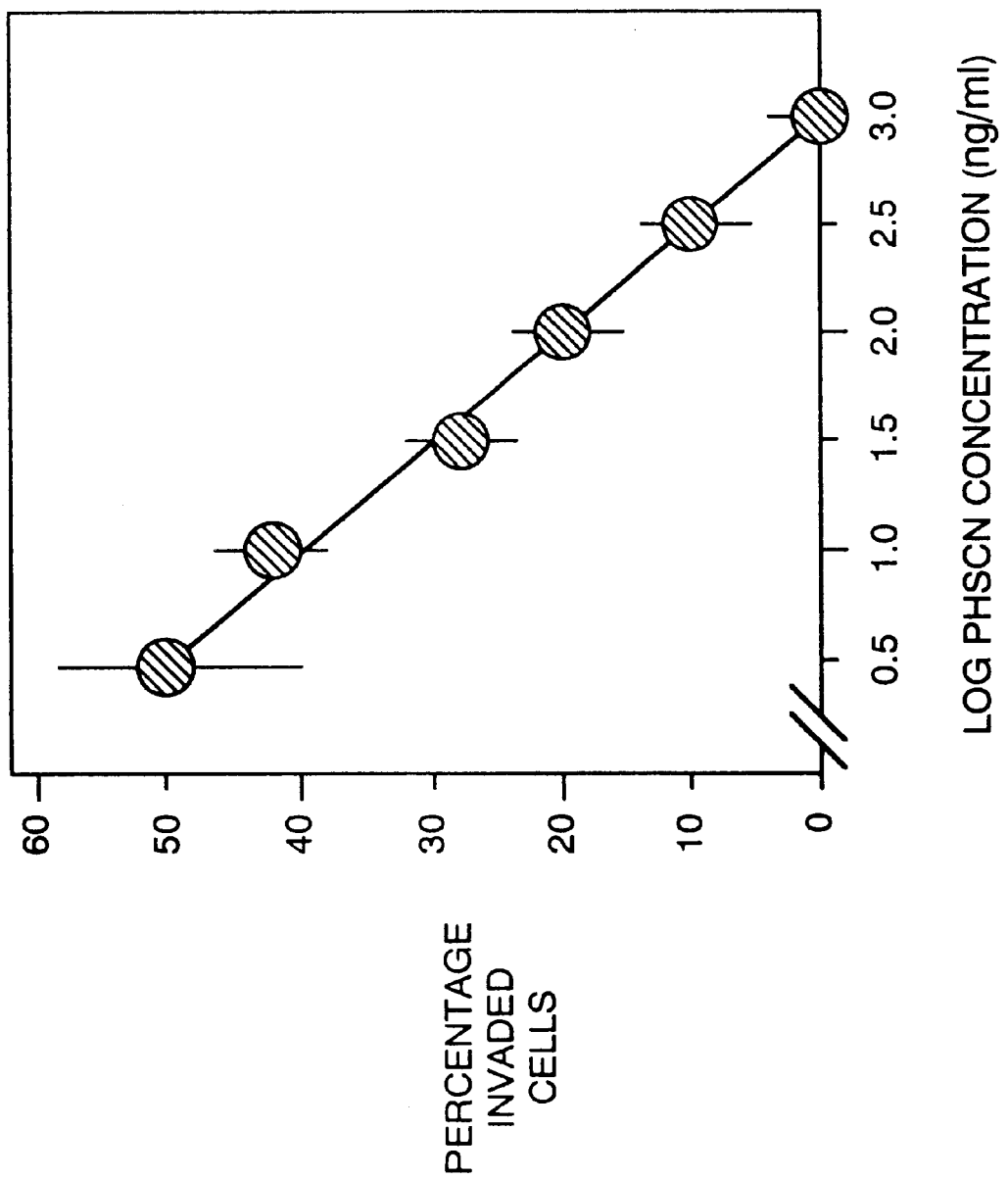

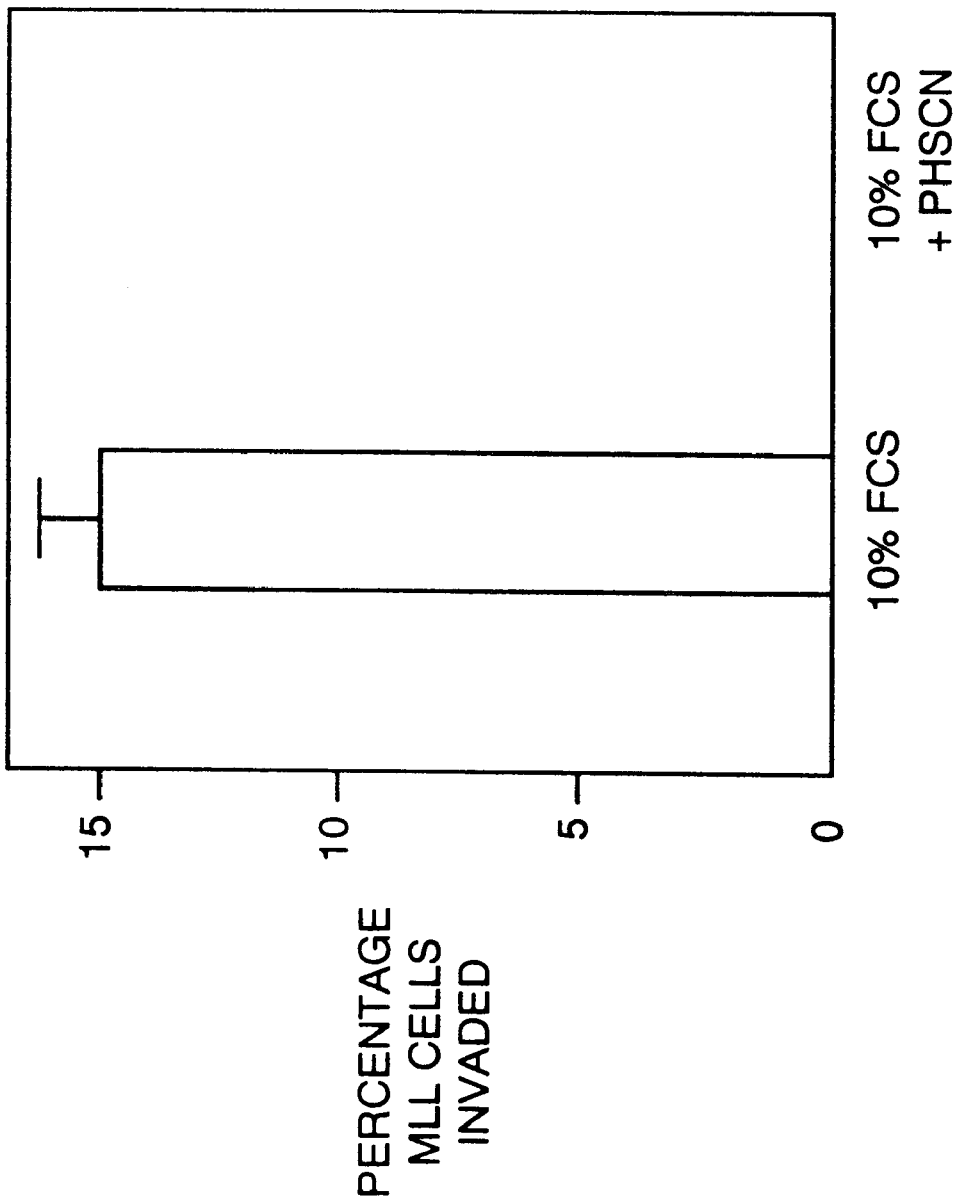

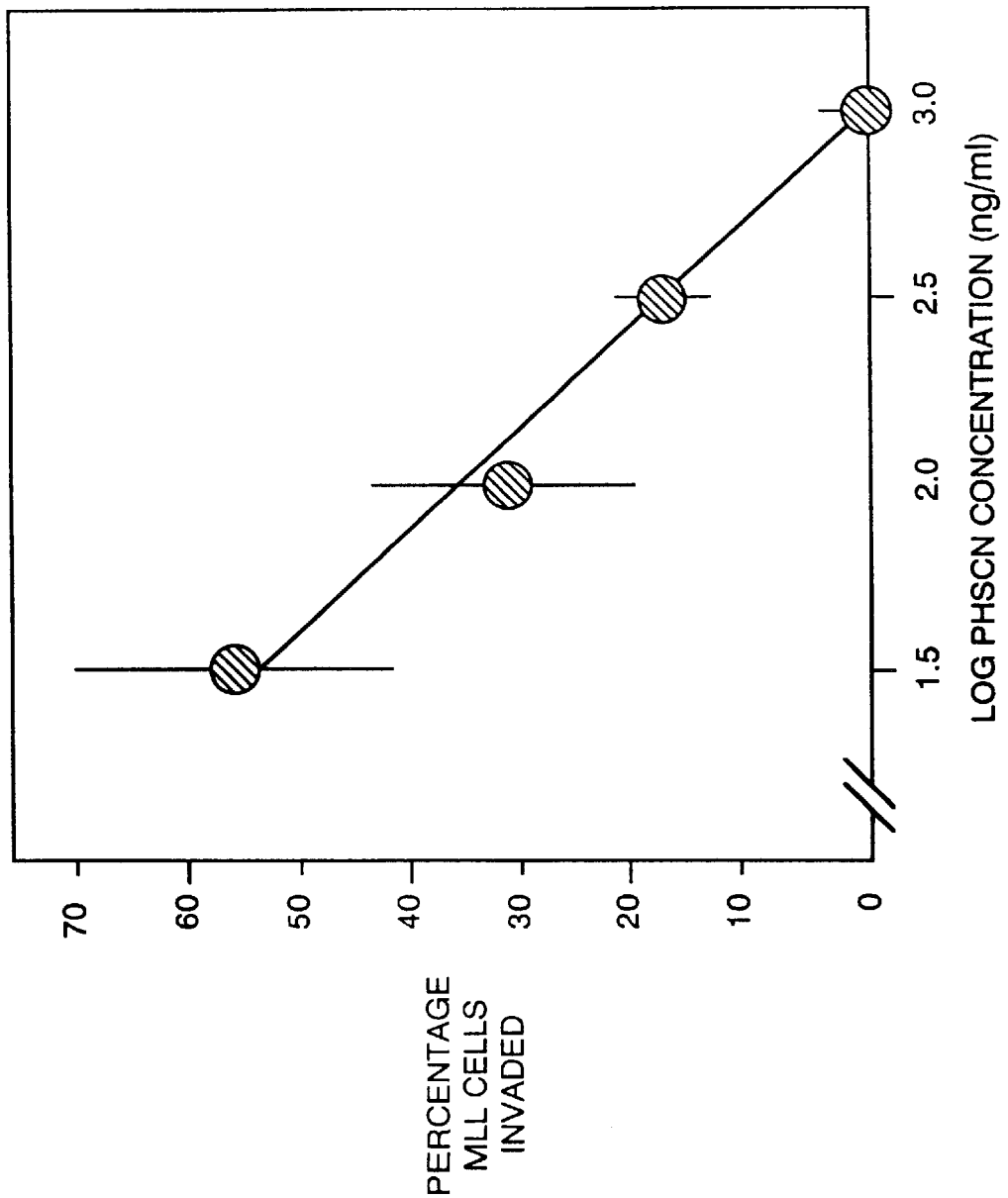

ANTICANCER COMPOUNDS AND METHODS

This application is a Continuation-In-Part of application Ser. No. 08/754,322, filed on Nov. 21, 1996, subsequently issued as U.S. Pat. No. 5,840,514 on Nov. 24, 1998.

FIELD OF THE INVENTION

The present invention relates to the treatment of cancer, to the testing of cancer cells for their ability to invade tissues and cause metastases, and to the identification and use of drugs to inhibit tumor invasion and growth.

BACKGROUND

The term "chemotherapy" simply means the treatment of disease with chemical substances. The father of chemotherapy, Paul Ehrlich, imagined the perfect chemotherapeutic as a "magic bullet"; such a compound would kill invading organisms without harming the host. This target specificity is sought in all types of chemotherapeutics, including anticancer agents.

However, specificity has been the major problem with anticancer agents. In the case of anticancer agents, the drug needs to distinguish between host cells that are cancerous and host cells that are not cancerous. The vast bulk of anticancer drugs are indiscriminate at this level. Typically anticancer agents have negative hematological effects (e.g., cessation of mitosis and disintegration of formed elements in marrow and lymphoid tissues), and immunosuppressive action (e.g., depressed cell counts), as well as a severe impact on epithelial tissues (e.g., intestinal mucosa), reproductive tissues (e.g., impairment of spermatogenesis), and the nervous system. P. Calabresi and B. A. Chabner, In: Goodman and Gilman *The Pharmacological Basis of Therapeutics* (Pergamon Press, 8th Edition) (pp. 1209–1216).

Success with chemotherapeutics as anticancer agents has also been hampered by the phenomenon of multiple drug resistance, resistance to a wide range of structurally unrelated cytotoxic anticancer compounds. J. H. Gerlach et al., *Cancer Surveys*, 5:25–46 (1986). The underlying cause of progressive drug resistance may be due to a small population of drug-resistant cells within the tumor (e.g., mutant cells) at the time of diagnosis. J. H. Goldie and Andrew J. Coldman, *Cancer Research*, 44:3643–3653 (1984). Treating such a tumor with a single drug first results in a remission, where the tumor shrinks in size as a result of the killing of the predominant drug-sensitive cells. With the drug-sensitive cells gone, the remaining drug-resistant cells continue to multiply and eventually dominate the cell population of the tumor.

Finally, the treatment of cancer has been hampered by the fact that there is considerable heterogeneity even within one type of cancer. Some cancers, for example, have the ability to invade tissues and display an aggressive course of growth characterized by metastases. These tumors generally are associated with a poor outcome for the patient. And yet, without a means of identifying such tumors and distinguishing such tumors from non-invasive cancer, the physician is at a loss to change and/or optimize therapy.

What is needed is a specific anticancer approach that is reliable for a wide variety of tumor types, and particularly suitable for invasive tumors. Importantly, the treatment must be effective with minimal host toxicity.

SUMMARY OF THE INVENTION

The present invention relates to the treatment of cancer, to the testing of cancer cells for their ability to invade tissues and cause metastases, and to the identification and use of drugs to inhibit tumor invasion and growth. The present invention provides: A) an in vitro model for testing cancer cells and evaluating invasive potential; B) a screening assay for identifying drugs that inhibit tumor invasion; and C) chemotherapeutics for treating cancer.

A variety of assay formats are contemplated for testing the invasive potential of cancer cells. In one embodiment, a portion of a patient's tumor is obtained (e.g., by biopsy) and placed in tissue culture on a fibronectin-free substrate. Thereafter, the response of the tumor cells to fibronectin or a fibronectin-derived peptide is assessed. Where fibronectin induces invasion of the membrane, the tumor can be considered to have metastatic potential. Where there is no significant invasion of the membrane, the tumor can be considered (at that time) to be non-metastatic.

In one embodiment, the present invention contemplates a method of evaluating human cancer comprising: a) providing: i) a human cancer patient, ii) a fibronectin-free substrate, and iii) one or more invasion-inducing agents; b) obtaining cancer cells from said patient; c) contacting said cells ex vivo with said fibronectin-free substrate and one or more invasion-inducing agents; and d) detecting cancer cell invasion of said substrate. Preferably the cancer cells are cultured in serum-free culture media so as to essentially avoid introducing complicating factors. In one embodiment, the invasion-inducing agent is a peptide, said peptide comprising the sequence PHSRN SEQ ID NO:1. In a preferred embodiment the invasion inducing agent is intact fibronectin.

While not limited to any mechanism, it is believed that cells exposed to invasion-inducing agents in this manner are potentially rendered capable of invading the substrate. Indeed, the present invention contemplates stimulation of invasion by all cells of the body, including, but not limited to: epithelial (keratinocytes, mammary and prostate epithelial), connective tissue (fibroblasts), and muscle (myoblast) cells. Again, while not limited to any mechanism, it is believed that the invasion inducing agent comprising the sequence PHSRN SEQ ID NO:1 binds to the $\alpha 5\beta 1$ receptor on the cancer cell and thereby induces invasion of the substrate. In this regard, the present invention provides a method of testing human cancer cells comprising: a) providing: i) a human cancer patient, ii) a fibronectin-free substrate, and iii) one or more invasion-inducing agents; b) obtaining $\alpha 5\beta 1$ integrin fibronectin receptor-expressing cancer cells from said patient; c) culturing said cells in serum-free culture media on said substrate in the presence of said invasion-inducing agents; and d) detecting cancer cell invasion of said substrate.

As noted above, the present invention also contemplates a screening assay for identifying drugs that inhibit tumor invasion. The present invention contemplates a screening assay utilizing the binding activity of fibronectin-derived peptides. In one embodiment, an inducible tumor cell line is placed in tissue culture on a fibronectin-free substrate. Thereafter, as an inducible tumor cell line, the tumor will be induced (under ordinary conditions) by fibronectin or the fibronectin-derived peptide to invade the substrate. However, in this drug screening assay, candidate drug inhibitors are added to the tissue culture (this can be done individually or in mixtures). Where the inducible tumor cell is found to be inhibited from invading the substrate, a drug inhibitor is indicated.

It is not intended that the present invention be limited by the nature of the drugs screened in the screening assay of the present invention. A variety of drugs, including peptides, are contemplated.

Finally, the present invention contemplates chemotherapeutics for treating invasive tumors. Specifically, a variety of anti-invasive chemotherapeutic agents are contemplated to antagonize the invasion-promoting activity of the PHSRN SEQ ID NO:1 peptide. In the preferred embodiment, the anti-invasive agent is a peptide with the amino acid sequence PHSCN SEQ ID NO:86. In another embodiment, the anti-invasive agent is a peptide which has an amino acid sequence comprising a sequence selected from the group consisting of CHSRN SEQ ID NO:87, PCSRN SEQ ID NO:88, PHCRN SEQ ID NO:89, and PHSRC SEQ ID NO:90. In another embodiment, the anti-invasive agent is a peptide which has an amino acid sequence comprising PHSXN SEQ ID NO:91, where X is an amino acid selected from the group consisting of homo-cysteine, the D-isomer of cysteine, histidine, or penicillamine.

The present invention also contemplates an anti-invasive agent comprising the amino acid sequence $X_1HSX_2N$ SEQ ID NO:92, wherein $X_1$ is either proline, histidine, or not an amino acid, and $X_2$ is an amino acid selected from the group consisting of the L-isomer of cysteine, the D-isomer of cysteine, homo-cysteine, histidine, or penicillamine. In another embodiment, the present invention contemplates an anti-invasive agent comprising the amino acid sequence $X_1X_2X_3X_4X_5$ SEQ ID NO:93, wherein $X_1$ is an amino acid selected from the group consisting of proline, glycine, valine, histidine, isoleucine, phenylalanine, tyrosine, and tryptophan, and $X_2$ is an amino acid selected from the group consisting of histidine, proline, tyrosine, asparagine, glutamine, arginine, lysine, phenylalanine, and tryptophan, and $X_3$ is an amino acid selected from the group consisting of serine, threonine, alanine, tyrosine, leucine, histidine, asparagine, and glutamine, and $X_4$ is an amino acid selected from the group consisting of cysteine, homo-cysteine, penicillamine, histidine, tyrosine, asparagine, glutamine, and methionine, and $X_5$ is an amino acid selected from the group consisting of asparagine, glutamine, serine, threonine, histidine, and tyrosine. In the preferred embodiment the peptide is PHSCN SEQ ID NO:86, where the cysteine is the L-isomer.

It is further contemplated that the anti-invasive agents named above comprise the named amino acid sequence and additional amino acids added to the amino terminus, the carboxyl terminus, or both the amino and carboxyl termini. In one embodiment, the anti-invasive agent is up to five hundred amino acids in length. It is also contemplated that, in some embodiments, the anti-invasive agents named above comprise a peptide with the amino terminus blocked by standard methods to prevent digestion by exopeptidases, for example by acetylation; and the carboxyl terminus blocked by standard methods to prevent digestion by exopeptidases, for example, by amidation.

In this regard, the present invention provides a method of treating cancer comprising: a) providing: i) a subject having cancer, and ii) a composition of matter comprising a peptide which inhibits the tumor invasion-promoting activity of the PHSRN SEQ ID NO:1 sequence of plasma fibronectin; and b) administering said composition to said subject. The present invention further contemplates using antagonists before and/or after surgical removal of the primary tumor. In one embodiment, the method comprises administering a PHSRN SEQ ID NO:1 antagonist as adjunct therapy with additional chemotherapeutics.

While not limited to any mechanism, it is believed that these anti-invasive chemotherapeutic agents antagonize the invasion-promoting activity of the PHSRN SEQ ID NO:1 sequence (e.g., of fibronectin) by blocking the binding of this sequence to its receptor on tumor cells. Again, while not limited to any mechanism, it is believed that the PHSRN SEQ ID NO:1 sequence may promote invasion by acting to displace a divalent cation (Mg+2, Ca+2, or Mn+) in the α5β1 receptor on metastatic tumor cells, and the above named chemotherapeutic anti-invasive agents might act to inhibit this invasion by chelating one or more of these divalent cations.

In another embodiment, the present invention contemplates anti-invasion antagonists to the IKVAV SEQ ID NO:2 sequence of laminin, including but not limited to, peptides comprising the structure, ICVAV SEQ ID NO:94, and corresponding peptide mimetics.

DESCRIPTION OF THE FIGURES

FIG. 6A is a graph showing the results of inhibiting serum-induced human prostate cancer cell invasion of the SU-ECM substrate with varying concentrations of the PHSCN SEQ ID NO:86 peptide.

FIG. 7A is a graph showing the results of testing serum-induced rat prostate cancer cell invasion of the SU-ECM substrate with and without the PHSCN SEQ ID NO:86 peptide.

FIG. 7B is a graph showing the results of inhibiting PHSRN (SEQ ID NO:1)-induced rat prostate cancer cell invasion of the SU-ECM substrate with varying concentrations of the PHSCN SEQ ID NO:86 peptide.

FIG. 9B is a graph showing the results of determining the mean number of lung metastases in the two groups of rats described in FIG. 9a.

FIG. 10B is a graph showing the results of determining the mean number of lung metastases in the two groups of rats described in FIG. 10a.

FIG. 10C is a graph showing the results of determining the mean mass of intraperitoneal metastatic tissues in the two groups of rats described in FIG. 10a.

DEFINITIONS

Figure 1:
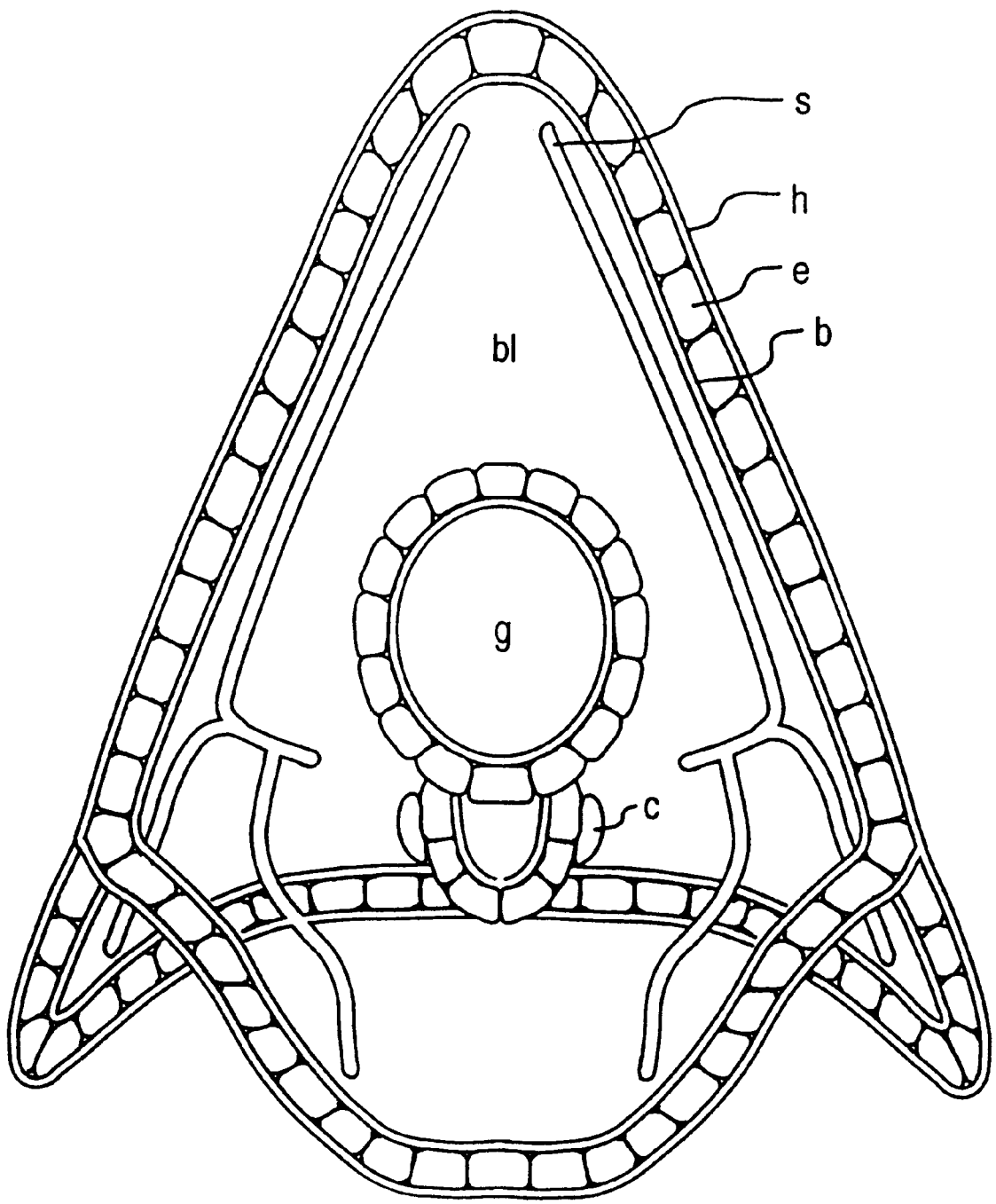
FIG. 1 schematically shows the one embodiment of the substrate used according to the present invention for testing tumor cells. The spatial relationship of the ectoderm of the *Strongylocentrotus purpuratus* embryo to its extracellular matrix and to blastocoelar structures are shown (s, spicules; h, hyalin layer; e, ectoderm; b, subectodermal basement membrane; bl, blastocoel; g, stomach of the primitive gut; c, coelomic pouches). The esophagus and intestine do not appear on the side of the embryo shown.

The term "drug" as used herein, refers to any medicinal substance used in humans or other animals. Encompassed within this definition are compound analogs, naturally occurring, synthetic and recombinant pharmaceuticals, hormones, antimicrobials, neurotransmitters, etc.

The term "inducing agent" refers to any compound or molecule which is capable of causing (directly or indirectly) the invasion of cells in a substrate. "Inducing agents" include, but are not limited to, PHSRN (SEQ ID NO:1)-containing peptides and related peptides (see below).

The term "receptors" refers to structures expressed by cells and which recognize binding molecules (e.g., ligands).

The term "antagonist" refers to molecules or compounds which inhibit the action of a "native" or "natural" compound (such as fibronectin). Antagonists may or may not be homologous to these natural compounds in respect to conformation, charge or other characteristics. Thus, antagonists may be recognized by the same or different receptors that are recognized by the natural compound. "Antagonists" include, but are not limited to, PHSCN (SEQ ID NO:86)-containing peptides and related peptides (see below).

The term "host cell" or "cell" refers to any cell which is used in any of the screening assays of the present invention. "Host cell" or "cell" also refers to any cell which either naturally expresses particular receptors of interest or is genetically altered so as to produce these normal or mutated receptors.

The term "chemotherapeutic agent" refers to molecules or compounds which inhibit the growth or metastasis of tumors. "Chemotherapeutics" include, but are not limited to, PHSCN (SEQ ID NO:86)-containing peptides and related peptides (see below).

As noted above, the present invention contemplates both the D and L isomers of cysteine which are identified collectively as "C".

The present invention also contemplates homo-cysteine, which is identified as "hC".

DESCRIPTION OF THE INVENTION

The present invention generally relates to the treatment of cancer, and more specifically, to the testing of cancer cells for their ability to invade tissues and cause metastases, and to the identification and use of drugs to inhibit tumor invasion and growth. As a prelude to metastasis, it is believed that cancer cells proteolytically alter basement membranes underlying epithelia or the endothelial linings of blood and lymphatic vessels, invade through the defects created by proteolysis, and enter the circulatory or lymphatic systems to colonize distant sites. During this process, the secretion of proteolytic enzymes is coupled with increased cellular motility and altered adhesion. After their colonization of distant sites, metastasizing tumor cells proliferate to establish metastatic nodules.

As noted above, chemotherapeutic agents are currently employed to reduce the unrestricted growth of cancer cells, either prior to surgical removal of the tumor (neoadjuvant therapy) or after surgery (adjuvant therapy). However, none of these methods has proved curative once metastasis has occurred. Since unrestricted invasive behavior is also a hallmark of metastatic tumor cells, methods for directly inhibiting tumor cell invasion and metastasis are needed.

A. Assays For Testing Tumor Invasion

Discovering how to inhibit the invasive behavior of tumor cells to intervene in the metastatic cascade first requires the development of assays with which to test tumor cell invasion in vitro. Two assay systems are contemplated for use in the method of the present invention to test the tumor cell invasion.

1. Fibronectin-Depleted Substrates

In one assay system, the present invention contemplates using fibronectin-depleted substrates. These are substrates that originally contain fibronectin that are treated according to the methods of the present invention (see below) to remove fibronectin. It is not intended that the present invention be limited by the nature of the original substrate; such fibronectin-containing substrates suitable for treatment and depletion include: i) complex substrates containing a variety of extracellular proteins and ii) less complex substrates containing fibronectin along with one or two other proteins (e.g., collagen, laminin, etc.).

It is also not intended that the present invention be limited by the precise amount of fibronectin remaining after the substrate has been treated. In other words, while the methods of the present invention remove fibronectin, and in some embodiments, remove substantially all fibronectin, it is within the meaning of the term "fibronectin-depleted" substrate that a small amount of fibronectin remain in the substrate.

In one embodiment, the present invention contemplates using an extracellular matrix available commercially. For example, the present invention contemplates treating basement membrane matrices such as ECM GEL, a matrix from mouse sarcoma (commercially available from Sigma, St. Louis, Mo.). However, it is not intended that the present invention be limited by the particular fibronectin-containing substrate. For example, other commercially available substrates are contemplated, such as the commonly used substrate Matrigel (available from Becton Dickinson Labware, Catalog #40234); Matrigel can be treated appropriately according to the methods of the present invention so as to render it "fibronectin-depleted" (see below). Untreated Matrigel (and similar substrates) have been used to demonstrate the importance of proteases and motility factors in the invasion and metastasis of many tumors. However, these invasion substrates are not available as serum-free substrates; thus, the regulation of tumor cell invasive behavior by serum components, such as plasma fibronectin, is a complicating factor with untreated Matrigel.

Consequently, the present invention contemplates a fibronectin-free substrate. In this embodiment, Matrigel is treated so that it is substantially fibronectin-free. The preparation of fibronectin-free Matrigel involves "panning" the Matrigel substrate on gelatin as well as "panning" the substrate on anti-fibronectin antibody (anti-human fibronectin IgG is available commercially, such as antibody from Promega Corporation, Madison, Wis.).

2. Naturally Occurring Fibronectin-Free Substrates

In another embodiment, the present invention contemplates substrates that are naturally free of fibronectin; such a source provides, for example, basement membranes permeable to select types of normally invasive cells, such membranes being naturally serum-free. In one embodiment, the present invention contemplates sea urchins as a source of such membranes. In this regard, the ectoderm of sea urchin embryos is one cell thick, and secretes an underlying basement membrane (see FIG. 1) very similar to that of mammals. These embryos contain no circulatory or lymphatic systems; and thus, their basement membranes are serum-free. In embryos, the subectodermal basement membrane functions simultaneously as a migration substrate for several, specific mesenchymal cell types while it functions as an invasion substrate for others. Sea urchin embryo basement membranes (SU-ECM) can be prepared by mild detergent treatment as described in D. Livant et al., *Cancer Research* 55:5085 (1995) and described in the Experimental section below.

Regardless of which of the two types of substrates are employed, the invasion substrates of the present invention are easy to prepare and give rapid, highly consistent results with a variety of cells, including: a) cell lines from: i) primary and metastatic tumors, and ii) normal epithelial tissues; as well as b) cells from primary tissue samples of both tumors, their surrounding normal tissues, and neonatal melanocytes, fibroblasts, and keratinocytes from circumcised tissue.

In one embodiment, the present invention contemplates a method of evaluating human cancer comprising: a) providing: i) a human cancer patient (such as a patient with breast cancer or prostate cancer), ii) a fibronectin-free substrate (for example, a fibronectin-depleted substrate) and iii) one or more invasion-inducing agents (discussed below); b) obtaining cancer cells from said patient (such as from a biopsy); c) contacting said cells ex vivo (i.e., outside the body) with said fibronectin-free substrate and said one or more invasion-inducing agents; and d) measuring the extent of cancer cell invasion of said substrate. Preferably the cancer cells are cultured in serum-free culture media so as to avoid introducing complicating factors.

3. Inducing Agents

It is not intended that the present invention be limited by the nature of the agent that causes or induces cells to invade the fibronectin-free substrates of the present invention. Such agents can be identified functionally by simply adding them to the cell culture and measuring the extent of invasion.

In one embodiment, the invasion-inducing agent comprises a peptide derived from fibronectin. In a preferred embodiment, the invasion inducing agent is intact fibronectin.

While not limited to any mechanism, it is believed that cells exposed to invasion-inducing agents in this manner are potentially rendered capable of invading the substrate. Again, while not limited to any mechanism, it is believed that the invasion inducing agent comprising the sequence PHSRN SEQ ID NO:1 binds to the α5β1 receptor on the cancer cell and thereby induces invasion of the substrate. In this regard, the present invention provides a method of treating cells comprising: a) providing: i) cells expressing the α5β1 receptor, ii) a fibronectin-free substrate, and iii) one or more invasion-inducing agents; b) culturing said cells in serum-free culture media on said substrate in the presence of said invasion-inducing agents; and d) measuring the extent of cell invasion of said substrate. In one embodiment, the cells are normal epithelial cells or fibroblasts. In another embodiment, the cells are human cancer cells.

B. Drug Screening Assays

The present invention also contemplates a screening assay for identifying drugs that inhibit tumor invasion. The present invention contemplates a screening assay (in the presence and absence of serum) utilizing the binding activity of fibronectin-derived peptides. In one embodiment, an inducible tumor cell line is placed in tissue culture on a fibronectin-free substrate. The tumor cells will be induced (under ordinary conditions) by the fibronectin-derived peptide to invade the substrate.

In one embodiment, the invasion-inducing agent comprises a peptide derived from fibronectin. In a preferred embodiment, said peptide comprises the sequence PHSRN SEQ ID NO:1. Of course, the peptide may be larger than five amino acids; indeed, the peptide fragment of fibronectin may contain hundreds of additional residues (e.g., five hundred amino acids). One such larger peptide is set forth in U.S. Pat. No. 5,492,890 (hereby incorporated by reference). In one embodiment, the PHSRN (SEQ ID NO:1)-containing peptide is less than one hundred amino acids in length and lacks the RGD SEQ ID NO:81 sequence characteristic of fibronectin. A variety of PHSRN (SEQ ID NO:1)-containing peptides are contemplated, including the PHSRN SEQ ID NO:1 peptide itself and related peptides where additional amino acids are added to the carboxyl terminus, including (but not limited to) peptides comprising the sequence: 1) PHSRN SEQ ID NO:1, 2) PHSRNS SEQ ID NO:3, 3) PHSRNSI SEQ ID NO:4, 4) PHSRNSIT SEQ ID NO:5, 5) PHSRNSITL SEQ ID NO:6, 6) PHSRNSITLT SEQ ID NO:7, 7) PHSRNSITLTN SEQ ID NO:8, 8) PHSRNSITLTNL SEQ ID NO:9, 9) PHSRNSITLTNLT SEQ ID NO:10, 10) PHSRNSITLTNLTP SEQ ID NO:11, and 11) PHSRNSITLTNLTPG SEQ ID NO:12. Alternatively, PHSRN (SEQ ID NO:1)-containing peptides are contemplated where amino acids are added to the amino terminus, including (but not limited to) peptides comprising the sequence: 1) PEHFSGRPREDRVPHSRN SEQ ID NO:13, 2) EHFSGRPREDRVPHSRN SEQ ID NO:14, 3) HFSGRPREDRVPHSRN SEQ ID NO:15, 4) FSGRPREDRVPHSRN SEQ ID NO:16, 5) SGRPREDRVPHSRN SEQ ID NO:17, 6) GRPREDRVPHSRN SEQ ID NO:18, 7) RPREDRVPHSRN SEQ ID NO:19, 8) PREDRVPHSRN SEQ ID NO:20, 9) REDRVPHSRN SEQ ID NO:21, 10) EDRVPHSRN SEQ ID NO:22, 11) DRVPHSRN SEQ ID NO:23, 12) RVPHSRN SEQ ID NO.:24, and 13) VPHSRN SEQ ID NO.:25. Finally, the present invention contemplates PHSRN (SEQ ID NO.:1)-containing peptides where amino acids are added to both the amino and carboxyl termini, including (but not limited to) peptides comprising the sequence PEHFSGRPREDRVPHSRNSITLTNLTPG SEQ ID NO.:26, as well as peptides comprising portions or fragments of the PHSRN (SEQ ID NO:1)-containing sequence PEHFSGRPREDRVPHSRNSITLTNLTPG SEQ ID NO.:26.

Peptides containing variations on the PHSRN SEQ ID NO.:1 motif are contemplated. For example, the present invention also contemplates PPSRN (SEQ ID NO.:27)-containing peptides for use in the above-named assays. Such peptides may vary in length in the manner described above for PHSRN (SEQ ID NO.:1)-containing peptides. Alternatively, PPSRN SEQ ID NO.:27 may be used as a peptide of five amino acids.

Similarly, peptides comprising the sequence -HHSRN- SEQ ID NO.:28, -HPSRN-SEQ ID NO.:29, -PHTRN-SEQ ID NO.:30, -HHTRN-SEQ ID NO.:31, -HPTRN-SEQ ID NO.:32, -PHSNN-SEQ ID NO.:33, -HHSNN-SEQ ID NO.:34, -HPSNN-SEQ ID NO.:35, -PHTNN-SEQ ID NO.:36, -HHTNN-SEQ ID NO.:37, -HPTNN-SEQ ID NO.:38, -PHSKN-SEQ ID NO.:39, -HHSKN-SEQ ID NO.:40, -HPSKN-SEQ ID NO.:41, -PHTKN-SEQ ID NO.:42, -HHTKN-SEQ ID NO.:43, -HPTKN-SEQ ID NO.:44, -PHSRR-SEQ ID NO.:45, -HHSRR-SEQ ID NO.:46, -HPSRR-SEQ ID NO.:47, -PHTRR-SEQ ID NO.:48, -HHTRR-SEQ ID NO.:49, -HPTRR-SEQ ID NO.:50, -PHSNR-SEQ ID NO.:51, -HHSNR-SEQ ID NO.:52, -HPSNR-SEQ ID NO.:53, -PHTNR-SEQ ID NO.:54, -HHTNR-SEQ ID NO.:55, -HPTNR-SEQ ID NO.:56, -PHSKR-SEQ ID NO.:57, -HHSKR-SEQ ID NO.:58, -HPSKR-SEQ ID NO.:59, -PHTKR-SEQ ID NO.:60, -HHTKR-SEQ ID NO.:61, -HPTKR-SEQ ID NO.:62, -PHSRK-SEQ ID NO.:63, -HHSRK-SEQ ID NO.:64, -HPSRK-SEQ ID NO.:65, -PHTRK-SEQ ID NO.:66, -HHTRK-SEQ ID NO.:67, -HPTRK-SEQ ID NO.:68, -PHSNK-SEQ ID NO.:69, -HHSNK-SEQ ID NO.:70, -HPSNK-SEQ ID NO.:71, -PHTNK-SEQ ID NO.:72, -HHTNK-SEQ ID NO.:73, -HPTNK-SEQ ID NO.:74, -PHSKK-SEQ ID NO.:75, -HHSKK-SEQ ID NO.:76, -HPSKK-SEQ ID NO.:77, -PHTKK-SEQ ID NO.:78, -HHTKK-SEQ ID NO.:79, or -HPTKK-SEQ ID NO.:80 are contemplated by the present invention. Such peptides can be used as five amino acid peptides or can be part of a longer peptide (in the manner set forth above for PHSRN (SEQ ID NO.:1)-containing peptides).

In another embodiment, the present invention contemplates an inducing agent comprising the amino acid sequence $X_1X_2X_3X_4X_5$ SEQ ID NO.:93, wherein $X_1$ is an amino acid selected from the group consisting of proline, glycine, valine, histidine, isoleucine, phenylalanine, tyrosine, and tryptophan, and $X_2$ is an amino acid selected from the group consisting of histidine, proline, tyrosine, asparagine, glutamine, arginine, lysine, phenylalanine, and tryptophan, and $X_3$ is an amino acid selected from the group consisting of serine, threonine, alanine, tyrosine, leucine, histidine, asparagine, and glutamine, and $X_4$ is an amino acid selected from the group consisting of arginine, lysine, and histidine, and $X_5$ is an amino acid selected from the group consisting of asparagine, glutamine, serine, threonine, histidine, and tyrosine.

In this drug screening assay, candidate drug inhibitors are added to the tissue culture (this can be done individually or in mixtures). Where the inducible tumor cell is found to be inhibited from invading the substrate, a drug inhibitor is indicated (see Examples section below using the PHSCN SEQ ID NO.:86 peptide).

It is not intended that the present invention be limited by the nature of the drugs screened in the screening assay of the present invention. A variety of drugs, including peptides and non-peptide mimetics, are contemplated.

It is also not intended that the present invention be limited by the particular tumor cells used for drug testing. A variety of tumor cells (for both positive and negative controls) are contemplated (including but not limited to the cells set forth in Table 1 below).

C. Invasion-Inducing Agents And Antagonists

While an understanding of the mechanisms involved in metastatic cancer is not necessary to the successful practice of the present invention, it is believed that tumor cell invasion of basement membranes occurs at several points in the metastatic cascade: (1) when epithelial tumor cells (such as those of breast and prostate cancers) leave the epithelium and enter the stroma, (2) when tumor cells enter the circulatory or lymphatic systems, and (3) when tumor cells leave the circulatory or lymphatic systems to invade distant sites. Thus, intervention in the induction of tumor cell invasiveness by using a PHSRN SEQ ID NO.:1 antagonist, such as the PHSCN SEQ ID NO.:86 peptide, to block tumor cell receptors for this sequence is contemplated as a method for decreasing the rate of metastasis.

One advantage of this strategy is that leukocytes are the only normal cells known to invade tissues to carry out their functions, and relatively few leukocytes are invasive at a given time. Thus, relatively small doses of an anti-invasion antagonist which blocks the binding of PHSRN SEQ ID NO.:1 to its receptor are required. Also, other than some immunodepression, there should be relatively few side effects associated with anti-metastatic treatment using compounds designed to block the induction of invasion. The lack of debilitating side effects expected from anti-invasive therapy means that using it in combination with anti-proliferative agents would be uncomplicated, and that it could be used prior to surgery or even prophylactically to block tumor cell invasion and metastasis.

The IKVAV SEQ ID NO.:2 sequence of laminin, a prevalent insoluble protein of the extracellular matrix, is known to stimulate liver colonization by metastatic human colon cancer cells in athymic mice [see Bresalier et al., Cancer Research 55:2476 (1995)]. Since IKVAV SEQ ID NO.:2, like PHSRN SEQ ID NO.:1, contains a basic amino acid (K) which, by virtue of its positive charge, might also function to displace a divalent cation from its integrin receptor and stimulate invasion, the present invention contemplates applying the strategy of developing anti-invasion antagonists to the IKVAV SEQ ID NO.:2 sequence of laminin.

TABLE 1

Designation And Origin Of Human Cell Lines And Strains[1]

| Origin | Cell Lines or Strains |
|---|---|
| Colonic carcinoma | SW1116, HCT116, SKCO-1, HT-29, KM12C, KM12SM, KM12L4, SW480 |
| Pancreatic carcinoma | BxPC-3, AsPC-1, Capan-2, MIA PaCa-2, Hs766T |
| Colon adenoma | VaCo 235 |
| Lung carcinoma | A549 |
| Prostate carcinoma | PC-3, DU-145 |
| Breast carcinoma | 009P, 013T, SUM-52 PE |
| Lymphoma | Daudi, Raji |
| Breast epithelium | 006FA |
| Diploid fibroblast | HCS (human corneal stroma), MRC-5 |

[1]The SW1116, HT-29, SW480, Raji lymphoblastoid cells, and the pancreatic lines are obtained from the American Type Culture Collection.

1. Antagonists

It is not intended that the present invention be limited by the nature of the agent that inhibits tumor invasiveness. A variety of anti-invasive chemotherapeutics are contemplated to antagonize the invasion-promoting activity of the PHSRN SEQ ID NO.:1 sequence.

In the preferred embodiment, the anti-invasive agent is a peptide with the amino acid sequence PHSCN SEQ ID NO.:86. In another embodiment, the anti-invasive agent is a peptide which has an amino acid sequence comprising a sequence selected from the group consisting of CHSRN SEQ ID NO.:87, PCSRN SEQ ID NO.:88, PHCRN SEQ ID NO.:89, and PHSRC SEQ ID NO.:90. In another embodiment, the anti-invasive agent is a peptide which has an amino acid sequence comprising PHSXN SEQ ID NO.:91, where X is an amino acid selected from the group consisting of homo-cysteine, the D-isomer of cysteine, histidine, or penicillamine.

The present invention also contemplates an anti-invasive agent comprising the amino acid sequence $X_1HSX_2N$ SEQ ID NO.:92, wherein $X_1$ is either proline, histidine, or not an amino acid, and $X_2$ is an amino acid selected from the group consisting of the L-isomer of cysteine, the D-isomer of cysteine, homo-cysteine, histidine, or penicillamine. In another embodiment, the present invention contemplates an anti-invasive agent comprising the amino acid sequence $X_1X_2X_3X_4X_5$ SEQ ID NO.:93, wherein $X_1$ is an amino acid selected from the group consisting of proline, glycine, valine, histidine, isoleucine, phenylalanine, tyrosine, and tryptophan, and $X_2$ is an amino acid selected from the group consisting of histidine, proline, tyrosine, asparagine, glutamine, arginine, lysine, phenylalanine, and tryptophan, and $X_3$ is an amino acid selected from the group consisting of serine, threonine, alanine, tyrosine, leucine, histidine, asparagine, and glutamine, and $X_4$ is an amino acid selected from the group consisting of cysteine, homo-cysteine, penicillamine, histidine, tyrosine, asparagine, glutamine, and methionine, and $X_5$ is an amino acid selected from the group consisting of asparagine, glutamine, serine, threonine, histidine, and tyrosine. In the preferred embodiment the peptide is PHSCN SEQ ID NO.:86, where the cysteine is the L-isomer.

Similarly, peptides comprising the sequence -PSCN-SEQ ID NO.:102, -HSCN-SEQ ID NO.:96, -PSCN-SEQ ID NO.:102, -HTCN-SEQ ID NO.:99, -PTCN-SEQ ID NO.:105, -HSCN- SEQ ID NO.:96, -HSCN-SEQ ID NO.:96, -PSCN-SEQ ID NO.:102, -HTCN-SEQ ID NO.:99, HTCN-SEQ ID NO.:99, -PTCN-SEQ ID NO.:105, -HSCN- SEQ ID NO.:96, -HSCN-SEQ ID NO.:96, -PSCN-SEQ ID NO.:102, -HTCN-SEQ ID NO.:99, -HTCN-SEQ ID NO.:99, -PTCN-SEQ ID NO.:105, -HSCR-SEQ ID NO.:97, -HSCR-SEQ ID NO.:97, -PSCR-SEQ ID NO.:103, -HTCR-SEQ ID NO.:100, -HTCR-SEQ ID NO.:100, -PTCR-SEQ ID NO.:106, -HSCR-SEQ ID NO.:97, -HSCR-SEQ ID NO.:97, -PSCR-SEQ ID NO.:103, -HTCR-SEQ ID NO.:100, -HTCR-SEQ ID NO.:100, -PTCR-SEQ ID NO.:106, -HSCR-SEQ ID NO.:97, -HSCR-SEQ ID NO.:97, -PSCR-SEQ ID NO.:103, -HTCR-SEQ ID NO.:100, -HTCR-SEQ ID NO.:100, -PTCR-SEQ ID NO.:106, -HSCK-SEQ ID NO.:95, -HSCK-SEQ ID NO.:95, -PSCK-SEQ ID NO.:101, -HTCK-SEQ ID NO.:98, -HTCK-SEQ ID NO.:98, -PTCK-SEQ ID NO.:104, -HSCK-SEQ ID NO.:95, -HSCK-SEQ ID NO.:95, -PSCK-SEQ ID NO.:101, -HTCK-SEQ ID NO.:98, -HTCK-SEQ ID NO.:98, -PTCK-SEQ ID NO.:104, -HSCK-SEQ ID NO.:95, -HSCK-SEQ ID NO.:95, -PSCK-SEQ ID NO.:101, -HTCK-SEQ ID NO.:98, -HTCK-SEQ ID NO.:98, or -PTCK-SEQ ID NO.:104 are contemplated by the present invention.

It is further contemplated that, in some embodiments, the anti-invasive agents named above comprise the named amino acid sequence and additional amino acids added to the amino terminus, the carboxyl terminus, or both the amino and carboxyl termini (in the manner set forth above for the PHSRN SEQ ID NO.:1 containing peptides, e.g., PHSRNSIT SEQ ID NO.:5). In one embodiment, the anti-invasive agent is up to five hundred amino acids in length. It is also contemplated that, in some embodiments, the anti-invasive agents named above comprise a peptide with the amino terminus blocked by standard methods to prevent digestion by exopeptidases, for example by acetylation; and the carboxyl terminus blocked by standard methods to prevent digestion by exopeptidases, for example, by amidation.

In this regard, the present invention provides a method of treating cancer comprising: a) providing: i) a subject having cancer, and ii) a composition of matter comprising a peptide, peptide derivative, or peptide mimetic which inhibits the tumor invasion-promoting activity of a peptide comprising the amino acid sequence PHSRN SEQ ID NO.:1, and b) administering said composition to said subject. The present invention further contemplates using antagonists before and/or after surgical removal of the primary tumor. In one embodiment, the method comprises administering a PHSRN SEQ ID NO.:1 antagonist as adjunct therapy with additional chemotherapeutics.

While not limited to any mechanism, it is believed that these anti-invasive chemotherapeutic agents antagonize the invasion-promoting activity of the PHSRN SEQ ID NO.:1 sequence (e.g., of fibronectin) by blocking the binding of this sequence to its receptor on tumor cells. Again, while not limited to any mechanism, it is believed that the PHSRN SEQ ID NO.:1 sequence may promote invasion by acting to displace a divalent cation (Mg+2, Ca+2, or Mn+) in the α5β1 receptor on metastatic tumor cells, and the above named chemotherapeutic anti-invasive agents might act to inhibit this invasion by chelating one or more of these divalent cations.

In another embodiment, the present invention contemplates anti-invasion antagonists to the IKVAV SEQ ID NO.:2 sequence of laminin.

2. Designing Mimetics

Compounds mimicking the necessary conformation for recognition and docking to the receptor binding to the peptides of the present invention are contemplated as within the scope of this invention. For example, mimetics of PHSRN SEQ ID NO.:1 and PHSRN (SEQ ID NO.:1)-antagonists are contemplated. A variety of designs for such mimetics are possible. For example, cyclic PHSRN SEQ ID NO.:1 and PHSCN SEQ ID NO.:86 containing peptides, in which the necessary conformation for binding is stabilized by nonpeptides, are specifically contemplated. U.S. Pat. No. 5,192,746 to Lobl, et al., U.S. Pat. No. 5,169,862 to Burke, Jr., et al., U.S. Pat. No. 5,539,085 to Bischoff, et al., U.S. Pat. No. 5,576,423 to Aversa, et al., U.S. Pat. No. 5,051,448 to Shashoua, and U.S. Pat. No. 5,559,103 to Gaeta, et al., all hereby incorporated by reference, describe multiple methods for creating such compounds.

Synthesis of nonpeptide compounds that mimic peptide sequences is also known in the art. Eldred, et al., (*J. Med. Chem.* 37:3882 (1994)) describe nonpeptide antagonists that mimic the Arg-Gly-Asp sequence. Likewise, Ku, et al., (*J. Med. Chem.* 38:9 (1995)) give further elucidation of the synthesis of a series of such compounds. Such nonpeptide compounds that mimic PHSRN SEQ ID NO.:1 and PHSRN (SEQ ID NO.:1)-antagonists are specifically contemplated by the present invention.

The present invention also contemplates synthetic mimicking compounds that are multimeric compounds that repeat the relevant peptide sequences. In one embodiment of the present invention, it is contemplated that the relevant peptide sequence is Pro-His-Ser-Arg-Asn SEQ ID NO.:1; in another embodiment, the relevant peptide sequence is Pro-His-Ser-Cys-Asn SEQ ID NO.:86; in another embodiment, the relevant peptide sequence is Ile-Lys-Val-Ala-Val SEQ ID NO.:2. As is known in the art, peptides can be synthesized by linking an amino group to a carboxyl group that has been activated by reaction with a coupling agent, such as dicyclohexylcarbodiimide (DCC). The attack of a free amino group on the activated carboxyl leads to the formation of a peptide bond and the release of dicyclohexylurea. It can be necessary to protect potentially reactive groups other than the amino and carboxyl groups intended to react. For example, the α-amino group of the component containing the activated carboxyl group can be blocked with a tertbutyloxycarbonyl group. This protecting group can be subsequently removed by exposing the peptide to dilute acid, which leaves peptide bonds intact.

With this method, peptides can be readily synthesized by a solid phase method by adding amino acids stepwise to a growing peptide chain that is linked to an insoluble matrix, such as polystyrene beads. The carboxyl-terminal amino acid (with an amino protecting group) of the desired peptide sequence is first anchored to the polystyrene beads. The protecting group of the amino acid is then removed. The next amino acid (with the protecting group) is added with the coupling agent. This is followed by a washing cycle. The cycle is repeated as necessary.

In one embodiment, the mimetics of the present invention are peptides having sequence homology to the above-described PHSRN SEQ ID NO.:1 sequences and PHSRN (SEQ ID NO.:1)-antagonists. One common methodology for evaluating sequence homology, and more importantly statistically significant similarities, is to use a Monte Carlo analysis using an algorithm written by Lipman and Pearson to obtain a Z value. According to this analysis, a Z value greater than 6 indicates probable significance, and a Z value greater than 10 is considered to be statistically significant. W. R. Pearson and D. J. Lipman, Proc. Natl. Acad. Sci. (USA), 85:2444–2448 (1988); D. J. Lipman and W. R. Pearson, Science, 227:1435–1441 (1985). In the present invention, synthetic polypeptides useful in tumor therapy and in blocking invasion arc those peptides with statistically significant sequence homology and similarity (Z value of Lipman and Pearson algorithm in Monte Carlo analysis exceeding 6).

3. Antibody Inhibitors

The present invention contemplates all types of inhibitors of tumor invasion for use in both the assays and for therapeutic use. In one embodiment, the present invention contemplates antibody inhibitors. The antibodies may be monoclonal or polyclonal, but polyclonal antibodies are often more effective inhibitors. It is within the scope of this invention to include any second antibodies (monoclonal or polyclonal) directed to the first antibodies discussed above. Both the first and second antibodies may be used in the detection assays or a first antibody may be used with a commercially available anti-immunoglobulin antibody. An antibody as contemplated herein includes any antibody specific to any region of a peptide involved in the induction of tumor cell invasion. For example, the present invention contemplates antibodies reactive with PHSRN SEQ ID NO.:1 peptides (as well as the related peptides set forth above).

Both polyclonal and monoclonal antibodies are obtainable by immunization with peptides, as well as with enzymes or proteins, and all types are utilizable for immunoassays. The methods of obtaining both types of sera are well known in the art. Polyclonal sera are less preferred but arc relatively easily prepared by injection of a suitable laboratory animal with an effective amount of the purified enzyme or protein, or antigenic parts thereof, collecting serum from the animal, and isolating specific sera by any of the known immunoadsorbent techniques. Although antibodies produced by this method are utilizable in virtually any type of immunoassay, they are generally less favored because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art. (See, for example Douillard and Hoffman, Basic Facts about Hybridomas, in *Compendium of Immunology* Vol II, ed. by Schwartz, 1981; Kohler and Milstein, *Nature* 256: 495–499, 1975; *European Journal of Immunology* 6: 511–519, 1976).

Unlike preparation of polyclonal sera, the choice of animal is dependent on the availability of appropriate immortal lines capable of fusing with lymphocytes. Mouse and rat have been the animals of choice in hybridoma technology and are preferably used. Humans can also be utilized as sources for sensitized lymphocytes if appropriate immortalized human (or nonhuman) cell lines are available. For the purpose of the present invention, the animal of choice may be injected with an antigenic amount, for example, from about 0.1 mg to about 20 mg of the enzyme or protein or antigenic parts thereof. Usually the injecting material is emulsified in Freund's complete adjuvant. Boosting injections may also be required. The detection of antibody production can be carried out by testing the antisera with appropriately labelled antigen. Lymphocytes can be obtained by removing the spleen of lymph nodes of sensitized animals in a sterile fashion and carrying out fusion. Alternatively, lymphocytes can be stimulated or immunized in vitro, as described, for example, in Reading, *Journal of Immunological Methods* 53: 261–291, 1982.

A number of cell lines suitable for fusion have been developed and the choice of any particular line for hybridization protocols is directed by any one of a number of criteria such as speed, uniformity of growth characteristics, deficiency of its metabolism for a component of the growth medium, and potential for good fusion frequency.

Intraspecies hybrids, particularly between like strains, work better than interspecies fusions. Several cell lines are available, including mutants selected for the loss of ability to secrete myeloma immunoglobulin.

Cell fusion can be induced either by virus, such as Epstein-Barr or Sendai virus, or polyethylene glycol. Polyethylene glycol (PEG) is the most efficacious agent for the fusion of mammalian somatic cells. PEG itself may be toxic for cells and various concentrations should be tested for effects on viability before attempting fusion. The molecular weight range of PEG may be varied from 1000 to 6000. It gives best results when diluted to from about 20% to about 70% (w/w) in saline or serum-free medium. Exposure to PEG at 37° C. for about 30 seconds is preferred in the present case, utilizing murine cells. Extremes of temperature (i.e., about 45° C.) are avoided, and preincubation of each component of the fusion system at 37° C. prior to fusion can be useful. The ratio between lymphocytes and malignant cells is optimized to avoid cell fusion among spleen cells and a range of from about 1:1 to about 1:10 is commonly used.

The successfully fused cells can be separated from the mycloma line by any technique known by the art. The most common and preferred method is to choose a malignant line which is Hypoxthanine Guanine Phosphoribosyl Transferase (HGPRT) deficient, which will not grow in an aminopterin-containing medium used to allow only growth of hybrids and which is generally composed of hypoxthanine $1\times10-4M$, aminopterin $1\times10-5M$, and thymidine $3\times10-5M$, commonly known as the HAT medium. The fusion mixture can be grown in the HAT-containing culture medium immediately after the fusion 24 hours later. The feeding schedules usually entail maintenance in HAT medium for two weeks and then feeding with either regular culture medium or hypoxthanine, thymidine-containing medium.

The growing colonies are then tested for the presence of antibodies that recognize the antigenic preparation. Detection of hybridoma antibodies can be performed using an assay where the antigen is bound to a solid support and allowed to react to hybridoma supernatants containing putative antibodies. The presence of antibodies may be detected by "sandwich" techniques using a variety of indicators. Most of the common methods are sufficiently sensitive for use in the range of antibody concentrations secreted during hybrid growth.

Cloning of hybrids can be carried out after 21–23 days of cell growth in selected medium. Cloning can be preformed by cell limiting dilution in fluid phase or by directly selecting single cells growing in semi-solid agarose. For limiting dilution, cell suspensions are diluted serially to yield a statistical probability of having only one cell per well. For the agarose technique, hybrids are seeded in a semi-solid upper layer, over a lower layer containing feeder cells. The colonies from the upper layer may be picked up and eventually transferred to wells.

Antibody-secreting hybrids can be grown in various tissue culture flasks, yielding supernatants with variable concentrations of antibodies. In order to obtain higher concentrations, hybrids may be transferred into animals to obtain inflammatory ascites. Antibody-containing ascites can be harvested 8–12 days after intraperitoneal injection. The ascites contain a higher concentration of antibodies but include both monoclonals and immunoglobulins from the inflammatory ascites. Antibody purification may then be achieved by, for example, affinity chromatography.

A wide range of immunoassay techniques are available for evaluating the antibodies of the present invention as can be seen by reference to U.S. Pat. Nos. 4,016,043; 4,424,279 and 4,018,653, hereby incorporated by reference. This, of course, includes both single-site and two-site, or "sandwich", assays of the non-competitive types, as well as in the traditional competitive binding assays.

4. Administering Chemotherapeutics

It is contemplated that the antagonists of the present invention be administered systemically or locally to inhibit tumor cell invasion in cancer patients with locally advanced or metastatic cancers. They can be administered intravenously, intrathecally, intraperitoneally as well as orally. PHSRN SEQ ID NO.:1 antagonists (e.g., the PHSCN SEQ ID NO.:86 peptide), can be administered alone or in combination with anti-proliferative drugs in a neoadjuvant setting to reduce the metastatic load in the patient prior to surgery; or they can be administered after surgery. Since PHSRN SEQ ID NO.:1 antagonists may depress wound healing (because the PHSRN SEQ ID NO.:1 sequence also elicits fibroblast invasion as described below), it may be necessary to use PHSRN SEQ ID NO.:1 antagonists some time after surgery to remove the tumor.

Since few cells in the body must invade in order to function, PHSRN SEQ ID NO.:1 antagonists administered systemically are not likely to cause the debilitating side effects of cytotoxic chemotherapeutic agents. However, since they suppress invasion, they are likely to cause some immunodepression. Even so, at the appropriate dosage, PSHRN SEQ ID NO.:1 antagonists may be administered prophylactically. In any case, it is contemplated that they may be administered in combination with cytotoxic agents. The simultaneous selection against the two fatal attributes of metastatic cells, unrestricted proliferation and invasion, is contemplated as a very powerful therapeutic strategy.

Where combinations are contemplated, it is not intended that the present invention be limited by the particular nature of the combination. The present invention contemplates combinations as simple mixtures as well as chemical hybrids. An example of the latter is where the antagonist is covalently linked to a targeting carrier or to an active pharmaceutical. Covalent binding can be accomplished by any one of many commercially available crosslinking compounds.

It is not intended that the present invention be limited by the particular nature of the therapeutic preparation. For example, such compositions can be provided together with physiologically tolerable liquid, gel or solid carriers, diluents, adjuvants and excipients.

These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual hosts.

Such compositions are typically prepared as liquid solutions or suspensions, or in solid forms. Oral formulations for cancer usually will include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%–95% of active ingredient, preferably 2%–70%.

The compositions are also prepared as injectables, either as liquid solutions or suspensions; solid forms suitable for solution in, or suspension in, liquid prior to injection may also be prepared.

The antagonists of the present invention are often mixed with diluents or excipients which are physiological tolerable and compatible. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents.

Additional formulations which are suitable for other modes of administration, such as topical administration, include salves, tinctures, creams, lotions, and, in some cases, suppositories. For salves and creams, traditional binders, carriers and excipients may include, for example, polyalkylene glycols or triglycerides.

Anti-Thrombotics

In addition to using the PHSRN SEQ ID NO.:1 antagonists described above as anti-invasion chemotherapeutics, it is also contemplated that these antagonists be used as anti-thrombotics. This use of the PHSRN SEQ ID NO.:1 antagonists described above is based on the discovery that PHSCN SEQ ID NO.:86 peptide-treated blood appears in vivo to clot very slowly.

A number of anti-thrombotic agents are currently known which inhibit clot formation by preventing platelet integrins from binding fibrinogen or fibronectin. These anti-thrombotics, however, rely on competitive inhibition to prevent platelet integrins from binding to fibrinogen or fibronectin. In this manner, large doses of these agents are required to achieve the desired anti-thrombotic affect.

The present invention contemplates a more effective approach using PHSRN (SEQ ID NO.:1)-antagonists such as PHSCN SEQ ID NO.:86. While the precise mechanism need not be known to practice the invention it has been shown that the platelet integrin, αIIbβ3, also binds the PHSRN SEQ ID NO.:1 sequence of plasma fibronectin. Thus, instead of utilizing competitive inhibition, the PHSRN (SEQ ID NO.:1)-antagonists may directly inhibit platelet integrins from binding fibronectin and aggregating. Specifically, the PHSCN SEQ ID NO.:86 peptide, or other PHSRN (SEQ ID NO.:1)-antagonists, may directly inhibit early stages in clot formation by binding to the αIIbβ3 receptors on platelets. This prevents platelet integrins from binding fibronectin, a necessary part of platelet aggregation, thus inhibiting an integral step in the blood clotting cascade. In this manner, a comparatively small dose of the PHSCN SEQ ID NO.:86 peptide, or other PHSRN SEQ ID NO.:1 antagonist, is contemplated as effective anti-thrombotic agents.

Wound Healing

As noted above, it is contemplated that PHSRN SEQ ID NO.:1 antagonists may depress wound healing. This expectation is based on the discovery that PHSRN (SEQ ID NO.:1)-containing peptides promote wound healing.

In this regard, it should be noted that the therapy of wounds, particularly those which are made difficult to heal by disease, has been attempted with a variety of purified growth factors or cytokines because these molecules can induce cellular proliferation or increase the motility of cells in wounds. Thus, if presented in the correct form and location at the right time, growth factors may greatly accelerate or enhance the healing of wounds by stimulating the growth of new tissue. Given the complexity and clinical variability of wounds, an obvious difficulty with the application of specific, purified growth factors or cytokines to wounded tissue, alone or in combination, is that their forms or specific distributions in the wound may not support their normal activities. Instead, the effectiveness of growth factors and cytokines in promoting the healing of wounded tissue may depend on their secretion by fibroblasts or macrophages.

The present invention contemplates a more effective approach; this approach involves methods that stimulate the invasion of the wound by the cells which synthesize the growth factors and cytokines active in stimulating wound repair, especially monocytes, macrophages, and fibroblasts. This strategy allows the cells in their normal in vivo setting to secrete the active factors. This approach has a number of advantages: (1) the temporal and spatial distributions of the factors are likely to be optimal because the normally active cells in their correct settings are secreting them; (2) all the appropriate factors are likely to be present in their active forms, irrespective of whether they have been identified or cloned; (3) the sequential effects of the factors in recruiting subsequent waves of cells involved in the healing process to the wound site are likely to be enhanced by the presence of more initiating cells in the wound.

The present invention is based on the discovery that the pure PHSRN SEQ ID NO.:1 peptide or purified plasma fibronectin fragments containing it, and lacking the α4β1 integrin binding site in the IIICS region, are sufficient to stimulate fibroblast invasion of basement membranes in vitro in the presence of serum or under serum-free conditions, while intact plasma fibronectin fails to stimulate fibroblast invasion. Pure PHSRN SEQ ID NO.:1 peptide has also been shown to stimulate keratinocyte invasion of serum-free SU-ECM. Since, during wound reepithelialization, keratinocytes migrate through the connective tissue of the provisional matrix to "wall off" portions of the wound, as well as through the adjacent stroma, it is not surprising that they are also stimulated to migrate through the matrix of SU-ECM invasion substrates by the PHSRN SEQ ID NO.:1 sequence. This suggests that this peptide, or proteinase-resistant forms of it, may have similar effects on fibroblasts, keratinocytes, and monocytes/macrophages in vivo. Recruitment of fibroblasts or monocytes/macrophages whose paracrine, regulatory effects on a variety of neighboring cells are required for the early stages of wound healing is contemplated as a highly efficient and effective way to stimulate the cascade of regulatory interactions involved in wound healing because these cells will secrete the active factors or cytokines in the correct temporal sequences and spatial locations to ensure their optimal activities. Because it efficiently induces keratinocyte migration through the extracellular matrix in vitro, the PHSRN SEQ ID NO.:1 peptide is also likely to stimulate wound reepithelialization directly. The use of the PHSRN SEQ ID NO.:1 peptide or structurally related molecules according to the present invention is to stimulate the entry of cells such as fibroblasts and monocyte/macrophages into the provisional matrix of a wound, so that the entering cells themselves secrete the factors and cytokines active in inducing or potentiating wound healing. The use of the PHSRN SEQ ID NO.:1 peptide or structurally related molecules is also intended to stimulate wound reepithelialization directly by inducing keratinocyte migration through the extracellular matrix.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); μM (micromolar); mM (millimolar); N (Normal); mol (moles); mmol (millimoles); μmol (micromoles); nmol (nanomoles); g (grams); mg (milligrams); μg (micrograms); L (liters); ml (milliliters); μl (microliters); cm (centimeters); mm (millimeters); μm (micrometers); nm (nanometers);° C. (degrees Centigrade); mAb (monoclonal antibody); MW (molecular weight); PBS (phophate buffered saline); U (units); d(days).

EXAMPLE 1

Production Of Fibronectin-Free Substrates

This example describes a purification approach for removal of plasma fibronectin (and/or cellular fibronectin) from a substrate (Matrigel). In this example, removal was attempted by affinity chromatography over Gelatin-Sepharose (a technique which can be used to remove plasma fibronectin from fetal calf serum).

The Gelatin-Sepharose beads were obtained from Pharmacia (Catalog# 17-0956-01). Two Kontes columns were set up with about 2 mls of Gelatin-Sepharose beads at 4° C. to prevent gelling of the Matrigel. The columns were then rinsed with about 10 column volumes of PBS to remove the preservative from the beads. The columns were drained to the top of the beads; then Matrigel was carefully added to the column. Once the Matrigel had entered the column, PBS was added to the top of the column. The Matrigel which was passed over the first column was collected and passed over the second column. The fibronectin-depleted Matrigel collected from the second column was plated on 48-well plates (150 μl/well), sterilized under a UV light for 10 minutes and incubated at 37° C. overnight. The Matrigel treated in this manner failed to form a gel at 37° C.

EXAMPLE 2

Production Of Fibronectin-Free Substrates

This example describes a purification approach for removal of plasma fibronectin (and/or cellular fibronectin) from a substrate (Matrigel). In this example, removal was attempted by successive panning on gelatin. Eight wells of 24-well plate were coated with a 2% gelatin solution (the gelatin was obtained from Becton Dickinson Labware, Catalog #11868). The wells were filled with the gelatin solution which had been heated to 50° C. and incubated for 3 minutes. Then the solution was removed and the wells were allowed to air dry. Following drying, the wells were thoroughly rinsed with ddH2O followed by two rinses with PBS. The plates were again allowed to dry; thereafter they were stored at −20° C. until use. Matrigel was thawed on ice and then added to one of the wells of a gelatin-coated plate (between 800 μl and 1 ml of Matrigel was added to a well of a 24-well plate). The plate was placed in a bucket of ice in a 4° C. room on an orbital shaker where the Matrigel was incubated in the well for two hours (although overnight incubation can be used). Following the incubation, the Matrigel was moved from the first well to a second well and then incubated for two hours under the same conditions. This process was repeated until the Matrigel had been incubated on all eight wells of the gelatin-coated plate.

Following the depletion of the Matrigel, it was collected in Eppendorf tubes. It was then plated on a 48-well plate 150 μl/well), sterilized under a UV light for 10 minutes and incubated at 37° C. overnight. The Matrigel formed as gel and the following day, cells were added to each well.

EXAMPLE 3

Production Of Fibronectin-Free Substrates

This example describes a purification approach for removal of plasma fibronectin (and/or cellular fibronectin) from a substrate (Matrigel). In this example, removal was attempted by gelatin panning followed by antibody panning.

Anti-fibronectin antibody-coated wells: Wells of a 24-well plate were coated with an anti-fibronectin antibody. A mouse monoclonal antibody to human fibronectin was obtained from Oncogene Science (Catalog #CP13). Each well was incubated with 1 ml of antibody at a concentration of 30 μl/ml for 2 hours at room temperature. Each well was then incubated with a solution of 3% BSA in PBS for 2 hours at room temperature. Following the two incubation periods, the wells were thoroughly washed with PBS and stored at −20° C. until use.

Depleting Matrigel of Fibronectin. Matrigel was panned over eight gelatin-coated wells (as described above in Example 2) to remove most of the fibronectin and its fragments. Thereafter, the Matrigel was placed in the antibody-coated wells to remove any remaining fragments of fibronectin which contain the cell-binding domain but not the gelatin-binding domain. The Matrigel was incubated in an ice bucket on an orbital shaker at 4° C. for 2 hours. Once the Matrigel was depleted, it was collected in Eppendorf tubes. The firbonectin-depleted Matrigel was plated on a 48-well plate (150 μl/well), sterilized under a UV light for 10 minutes and incubated at 37° C. overnight. The Matrigel formed a gel and the following day, cells were added to the wells.

EXAMPLE 4

Inducing Invasive Behavior Of Tumor Cells

In this example, the role of plasma fibronectin in inducing the invasive behaviors of metastatic breast and prostate cancer cells is demonstrated. Human breast carcinoma cell lines SUM 52 PE and SUM 44 PE were originally cultured from the pleural effusions of patients with metastatic breast cancer; and SUM 102 was cultured from a primary, microinvasive breast carcinoma (Ethier, S. P., Mahack, M. L., Gullick, W. J., Frank, T. S., and Weber, B. L. Differential isolation of normal luminal mammary epithelial cells and breast cancer cells from primary and metastatic sites using selective media. Cancer Res. 53: 627–635). The DU 145 metastatic human prostate cancer cell line was originally cultured from a brain metastasis (Stone, K. R., Mickey, D. D., Wunderli, H., Mickey, G. H., Paulsen, D. F. (1978) Isolation of a human prostate carcinoma cell line (DU 145), Int. J. Cancer 21: 274–281. These cells express α3β1 which has been shown to repress metalloproteinase transcription upon binding the connecting segment of plasma Fn. These cell lines can all be cultured under serum-free conditions; thus they are ideal for use in serum-free invasion assays on SU-ECM.

Adult *Strongylocentrotus purpuratus* sea urchins were obtained from Pacific BioMarine, and their embryos were cultured to the early pluteus stage in artificial sea water at 15° C. SU-ECM were prepared from them by treatment with nonionic detergent and srerilized by dilution in the appropriate media.

Cells were harvested by rinsing in Hanks' balanced salt solution, followed by brief treatment with 0.25% trypsin, 0.02% EDTA, and pelleting and resuspension in the appropriate medium with or without 5% FCS at a density of about 50,000 cells per ml. When appropriate, purified bovine plasma fibronectin (Sigma), purified 120 kDa chymotryptic fragment (Gibco BRL), PHSRN SEQ ID NO.:1 or PHSCN SEQ ID NO.:86 peptides (synthesized at the Biomedical Research Core Facilities of the University of Michigan), or GRGDSP SEQ ID NO.:83 or GRGESP SEQ ID NO.:84 peptides (Gibco BRL) were added to the resuspended cells prior to placement of the cells on SU-ECM. In each well of a plate used for an invasion assay, SU-ECM were placed in 0.5 ml of the appropriate medium, and 0.5 ml of the resuspended cells dropped on their exterior surfaces. Invasion assays were incubated 1 to 16 hours prior to assay. If some circumstances, invasion assays were fixed in phosphate-buffered saline (PBS) with 2% formaldehyde for 5 minutes at room temperature, then rinsed into PBS.

Invasion assays were coded and scored blindly by microscopic examination under phase contrast at 200- and 400-fold magnification. Each cell contacting an SU-ECM was scored for its position relative to the exterior or interior surfaces. A cell was judged to have invaded if it was located on an interior surface below the focal plane passing through the upper surface of the SU-ECM, but above the focal plane passing through its lower surface. The minimum viability of the cells in each assay was always ascertained at the time of assay by determining the fraction of spread, adherent cells on the bottom of each well scored.

An invasion frequency is defined as the fraction of cells in contact with basement membranes which were located in their interiors at the time of assay. Thus, an invasion frequency of 1 denotes invasion by 100% of the cells in contact with basement membranes. Invasion frequencies were determined multiple times for each cell type assayed. For each type of cell assayed the mean and standard deviation of the invasion frequencies were calculated.

The invasion-inducing sequences of plasma fibronectin were mapped to a peptide sequence 5 amino acids long, the PHSRN SEQ ID NO.:1 peptide, for both metastatic breast and prostate cancer cells. Since the PHSRN SEQ ID NO.:1 sequence is present in plasma fibronectin, a significant component of serum, eliciting the regulatory role of this sequence was only possible because of the availability of a serum-free in vitro invasion substrate. It should be noted that neonatal, human fibroblasts are also induced with the PHSRN SEQ ID NO.:1 peptide to invade serum-free SU-ECM. Although fibroblasts do not invade SU-ECM in the presence of serum, the 120 kDa fragment of plasma fibronectin containing the PHSRN SEQ ID NO.:1 sequence can induce fibroblast invasion equally well in the presence of serum or in its absence.

When taken together, the results of experiments showing that the PHSRN SEQ ID NO.:1 sequence of plasma fibronectin induces the invasive behaviors of both metastatic breast and prostate cancer cells, as well as that of normal fibroblasts suggest the intriguing possibility that the invasive behavior associated with tumor cell metastasis may result from defects in the regulation of the normal invasive behaviors associated with wound healing.

EXAMPLE 5

Testing Tumor Cells On Fibronectin-Depleted Substrates

Figure 2:
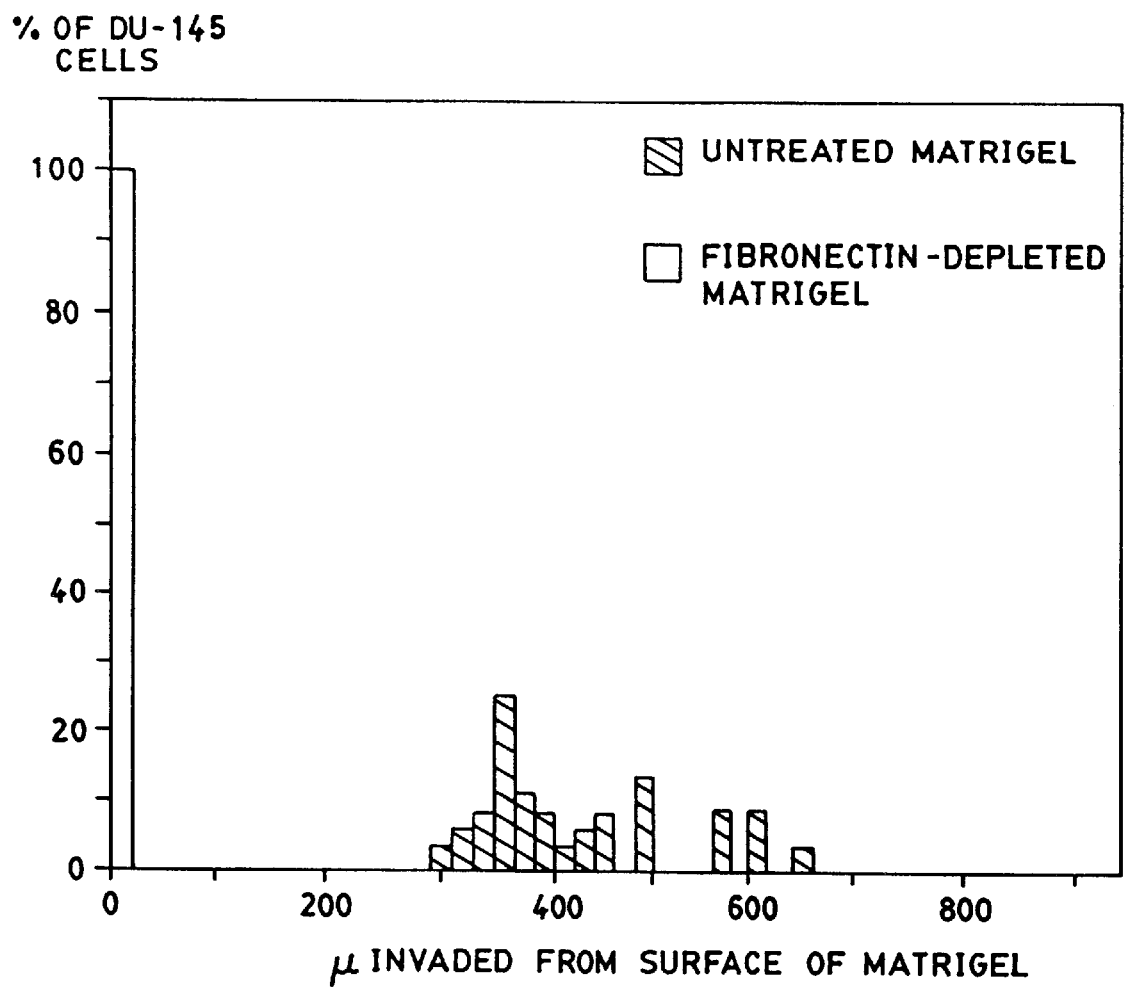
FIG. 2 is a graph showing the results of the testing of tumor cells on fibronectin-containing substrates and fibronectin-depleted substrates in vitro without the use of the invasion-inducing agents of the present invention.

This example describes an approach to test cancer cells in vitro on substrates with and without invasion-inducing agents. The depleted preparation of Matrigel (see Example 2, above) and untreated Matrigel were used to test DU-145 metastatic prostate cancer cells. When plated on the depleted medium, the cancer cells failed to invade the matrix (see FIG. 2). Indeed, it was evident that these cells were sitting on the surface of the depleted Matrigel because the Matrigel surface was slightly tilted; this was visible through the microscope as a gradual progressive, uniform change in the focal plane for the monolayer of DU-145 cells.

Figure 3:
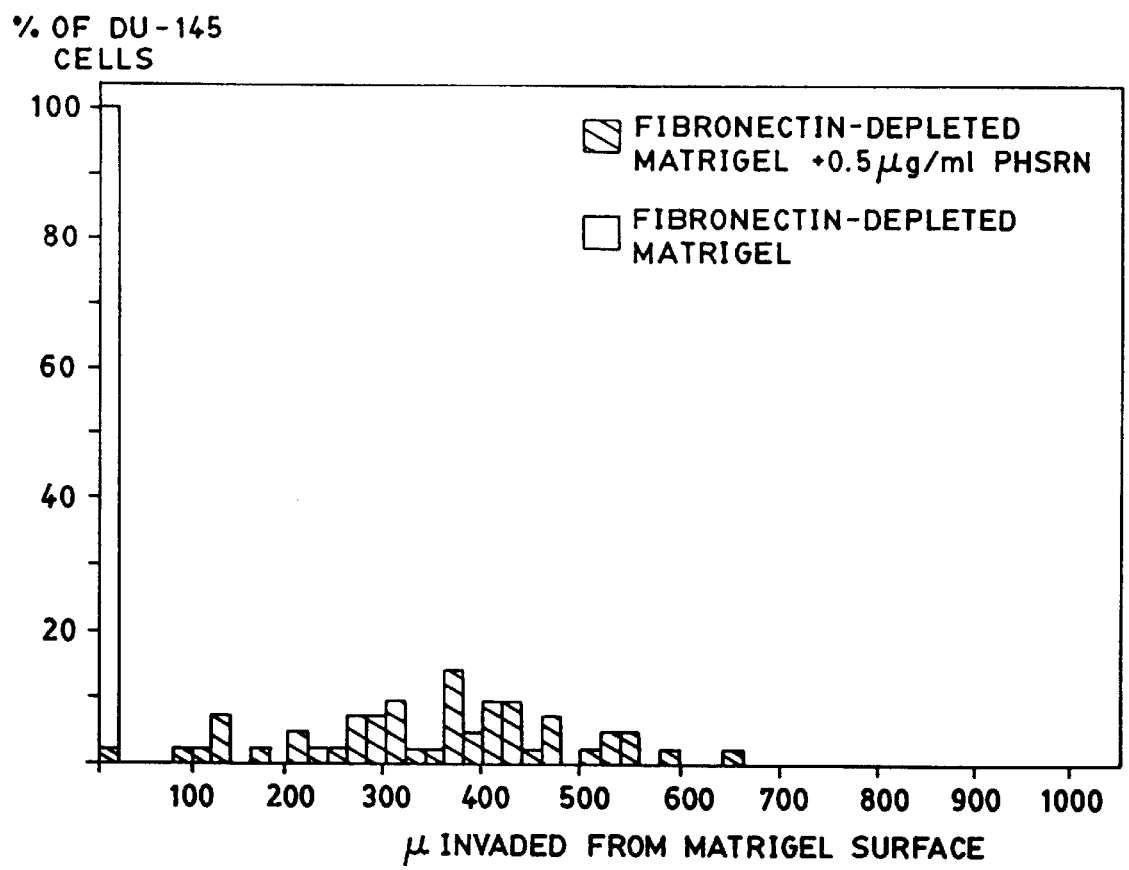
FIG. 3 is a graph showing the results of the testing of tumor cells on fibronectin-depleted substrates in vitro with and without invasion-inducing agents according one embodiment of the method of the present invention.

The addition of 0.5 $\mu$l/ml of the PHSRN SEQ ID NO.:1 peptide to the depleted Matrigel was sufficient to restore the full DU-145 invasiveness (see FIG. 3). Clearly, gelatin panning removes fibronectin such that cancer cells are unable to invade. Since the addition of PHSRN SEQ ID NO.:1 peptide in solution fully restores the DU-145 invasive phenotype, blocking the effect of PHSRN SEQ ID NO.:1 is an effective strategy for therapeutic intervention in tumor cell invasion and metastasis.

EXAMPLE 6

Improving Gelatin Depletion As Measured By Fibroblast Invasiveness

Figure 4:
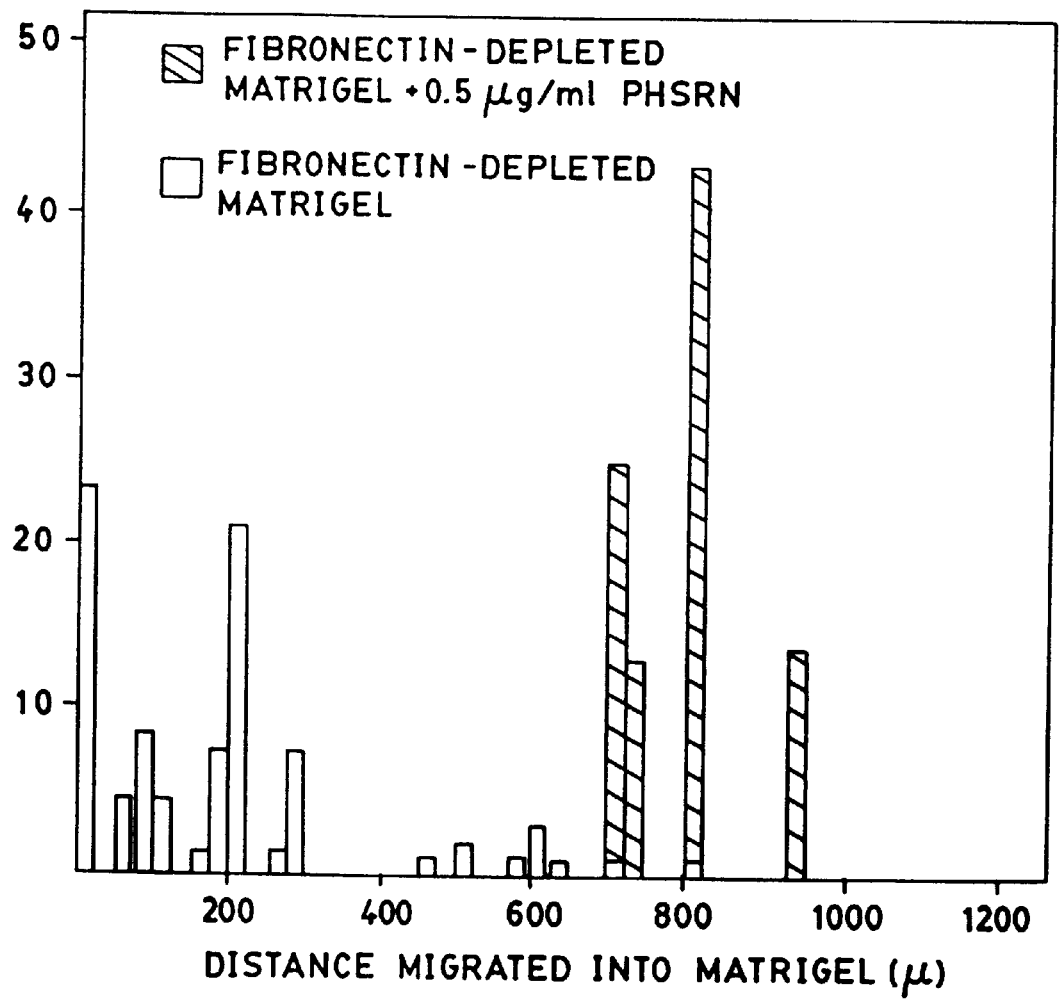
FIG. 4 is a graph showing the results of the testing of normal cells on fibronectin-depleted substrates in vitro with and without invasion-inducing agents according one embodiment of the method of the present invention.

In this example, normal, neonatal fibroblasts were tested on the depleted Matrigel material prepared according to Example 3 above (i.e., antibody depletion). As shown in FIG. 4, panning with an antibody after gelatin depletion improved the method for removal, as measured by the reduced invasiveness of fibroblasts. On the other hand, invasiveness of the fibroblasts could be induced by the addition of the PHSRN SEQ ID NO.:1 peptide.

The success of antibody panning suggests the feasibility of removing other components by the antibody panning methods. Other serum components, such as thrombospondin, growth factors and cytokines are contemplated by the present invention for removal by the appropriate (commercially available) antibody.

EXAMPLE 7

Conjugation Of PHSRN (SEQ ID NO.:1)-Containing Peptides

In this example, the preparation of a peptide conjugate is described. The synthetic peptide NH$_2$-PHSRNC SEQ ID NO.:82 can be prepared commercially (e.g., Multiple Peptide Systems, San Diego, Calif.). The cysteine is added to facilitate conjugation to other proteins.

In order to prepare a protein for conjugation (e.g., BSA), it is dissolved in buffer (e.g., 0.01 M NaPO$_4$, pH 7.0) to a final concentration of approximately 20 mg/ml. At the same time n-maleimidobenzoyl-N-hydroxysuccinimide ester ("MBS" available from Pierce) is dissolved in N,N-dimethyl formamide to a concentration of 5 mg/ml. The MBS solution, 0.51 ml, is added to 3.25 ml of the protein solution and incubated for 30 minutes at room temperature with stirring every 5 minutes. The MBS-activated protein is then purified by chromatography on a Bio-Gel P-10 column (Bio-Rad; 40 ml bed volume) equilibrated with 50 mM NaPO$_4$, pH 7.0 buffer. Peak fractions are pooled (6.0 ml).

The above-described cysteine-modified peptide (20 mg) is added to the activated protein mixture, stirred until the peptide is dissolved and incubated 3 hours at room temperature. Within 20 minutes, the reaction mixture becomes cloudy and precipitates form. After 3 hours, the reaction mixture is centrifuged at 10,000×g for 10 min and the supernatant analyzed for protein content. The conjugate precipitate is washed three times with PBS and stored at 4° C.

From the above, it should be clear that the present invention provides a method of testing a wide variety of tumor types, and in particular identifying invasive tumors. With a means of identifying such tumors (now provided by the present invention) and distinguishing such tumors from non-invasive cancer, the physician is able to change and/or optimize therapy. Importantly, the antagonists of the present invention (and other drugs developed by use of the screening assay of the present invention) will provide treatment directed an invasive cells (and therefore associated with minimal host toxicity).

EXAMPLE 8

Inhibiting Invasion Of Human Breast Cancer Cells

In this example, the role of the PHSCN SEQ ID NO.:86 peptide in inhibiting the invasive behavior of metastatic breast cancer cells is demonstrated. The method of Example 4 is employed, with the addition of varying concentrations of the PHSCN SEQ ID NO.:86 peptide.

Example 4 indicates that SUM-52 cells (in medium with 5% fecal calf serum) are induced to invade the SU-ECM substrate in the presence of serum fibronectin or just the PHSRN SEQ ID NO.:1 sequence of fibronectin. Thus, the procedure in Example 4 provides a method for determining the inhibitory potential of the PHSCN SEQ ID NO.:86 peptide by comparing the number of cell invasions in the presence of the PHSCN SEQ ID NO.:86 peptide, with the number of cell invasions in the absence of the PHSCN SEQ ID NO.:86 peptide.

Figure 5A:
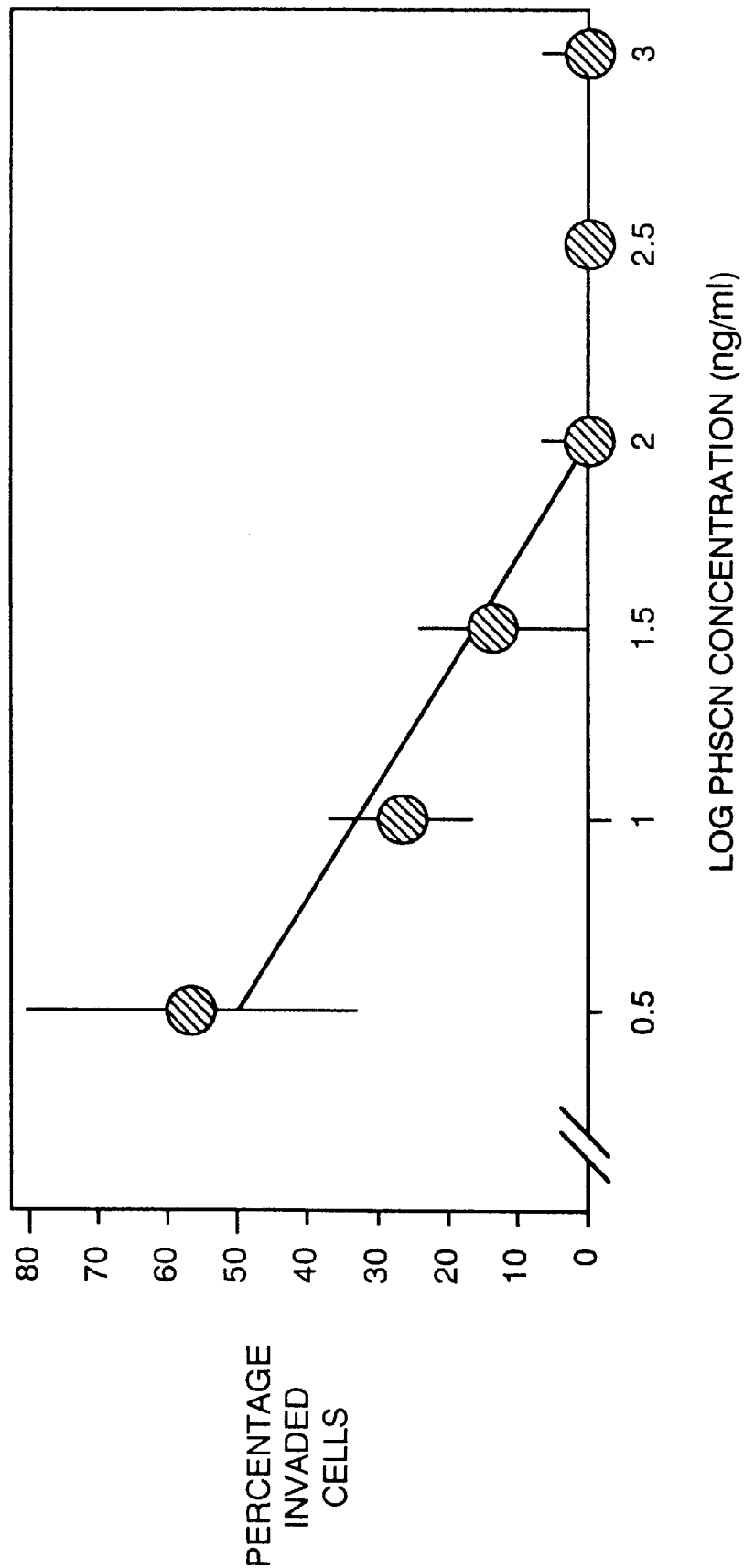
FIG. 5A is a graph showing the results of inhibiting serum-induced human breast cancer cell invasion of the SU-ECM substrate with varying concentrations of the PHSCN SEQ ID NO:86 peptide.

The results of adding varying concentrations of the PHSCN SEQ ID NO.:86 peptide to serum-induced invasion of metastatic SUM-52 PE breast cancer cells are presented in FIG. 5A. The logs of the PHSCN SEQ ID NO.:86 peptide concentrations in ng per ml are plotted on the X axis. The percentages of invaded SUM 52 PE cells relative to the percentage invaded in the absence of the PHSCN SEQ ID NO.:86 peptide are plotted on the Y axis. Mean invasion percentages are shown with their first standard deviations. Clearly, the PHSCN SEQ ID NO.:86 peptide exhibits a substantial inhibitory affect on these cells, even at relatively low concentrations. The PHSCN SEQ ID NO.:86 peptide's inhibitory affect is further demonstrated by the fact that relatively high concentrations cause complete inhibition.

Figure 5B:
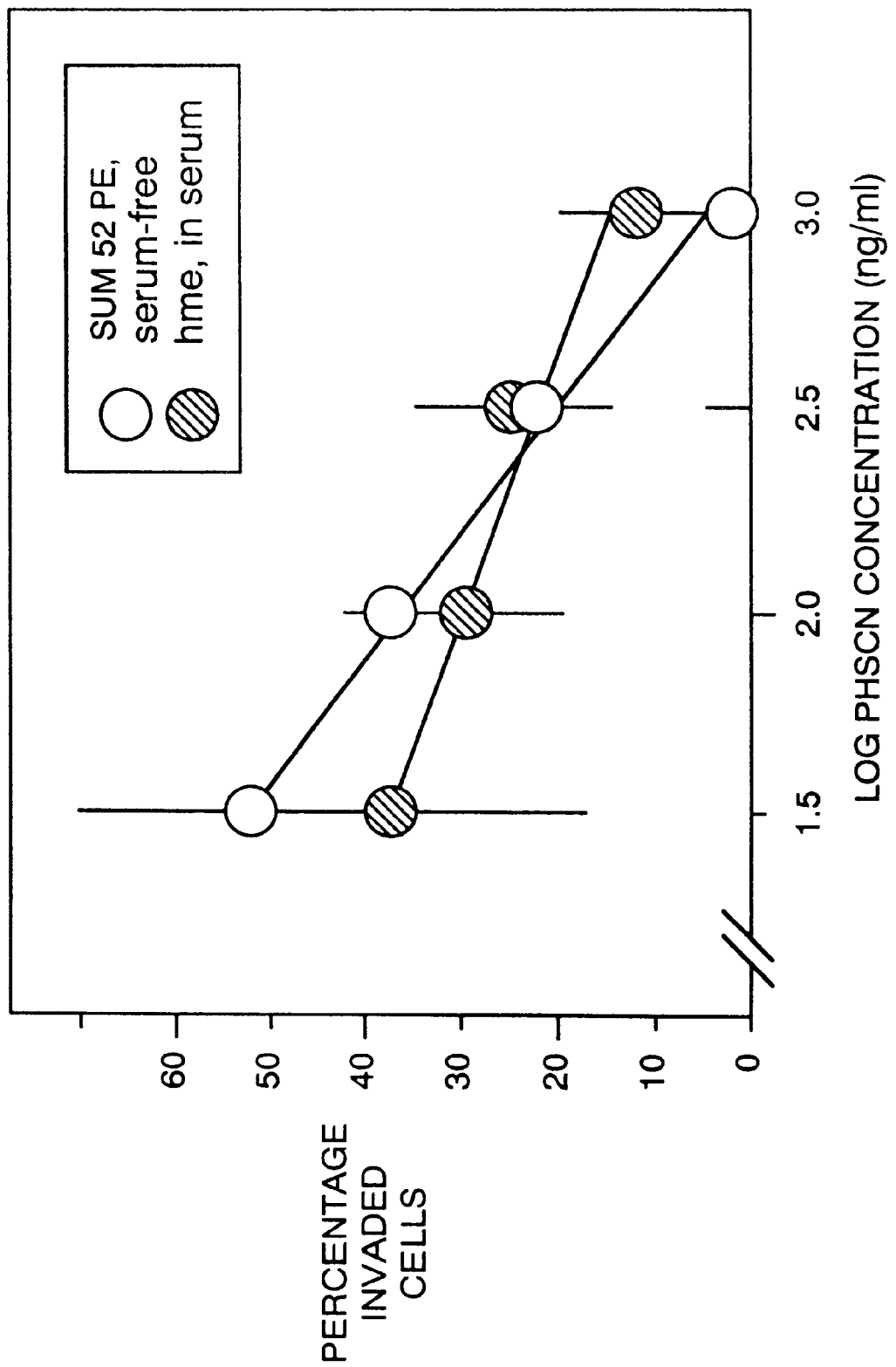
FIG. 5B is a graph showing the results of inhibiting PHSRN (SEQ ID NO:1)-induced invasion by both human breast cancer cells and normal human mammary epithelial cells of the SU-ECM substrate with varying concentrations of the PHSCN SEQ ID NO:86 peptide.

The results of adding varying concentrations of the PHSCN SEQ ID NO.:86 peptide to PHSRN (SEQ ID NO.:1)-induced invasion of both metastatic SUM-52 PE breast cancer cells (in serum free media) and normal human mammary epithelial cells (in 10% FCS), are presented in FIG. 5B. All invasion assays were carried out in 100 ng per ml of the PHSRN SEQ ID NO.:1 peptide to induce invasion. Again, the PHSCN SEQ ID NO.:86 peptide exhibits a substantial inhibitory affect on both cell lines at low concentrations, and almost complete inhibition at higher concentrations.

This example demonstrates the PHSCN SEQ ID NO:86 peptide is an effective inhibitor of human breast cancer cell invasion. In this manner, the PHSCN SEQ ID NO:86 peptide, or related sequences, are likely to provide effective therapy for human breast cancer by preventing the lethal affects of tumor cell metastasis.

EXAMPLE 9

Inhibiting Invasion Of Human Prostate Cancer Cells

In this example, the role of the PHSCN SEQ ID NO:86 peptide in inhibiting the invasive behavior of metastatic prostate cancer cells is demonstrated. The method of Example 4 is employed, with the addition of varying concentrations of the PHSCN SEQ ID NO:86 peptide.

Example 4 indicates that DU-145 cells are induced to invade the SU-ECM substrate in the presence of serum fibronectin or just the PHSRN SEQ ID NO:1 sequence of fibronectin. Thus, the procedure in Example 4 provides a method for determining the inhibitory potential of the PHSCN SEQ ID NO:86 peptide by comparing the number of cell invasions in the presence of the PHSCN SEQ ID NO:86 peptide, with the number of cell invasions in the absence of the PHSCN SEQ ID NO:86 peptide.

The results of adding varying concentrations of the PHSCN SEQ ID NO:86 peptide to serum-induced invasion of metastatic DU-145 prostate cancer cells (in 10% serum) are presented in FIG. 6A. The logs of the PHSCN SEQ ID NO:86 concentrations are plotted on the X axis. The percentages of invaded DU-145 cells relative to the percentage invaded in the absence of the PHSCN SEQ ID NO:86 peptide are plotted on the Y axis. Mean invasion percentages are shown with their first standard deviations. Clearly, the PHSCN SEQ ID NO:86 peptide exhibits a substantial inhibitory affect on these cells, even at relatively low concentrations. The PHSCN SEQ ID NO:86 peptide's inhibitory affect is further demonstrated by the fact that relatively high concentrations cause complete inhibition.

Figure 6B:
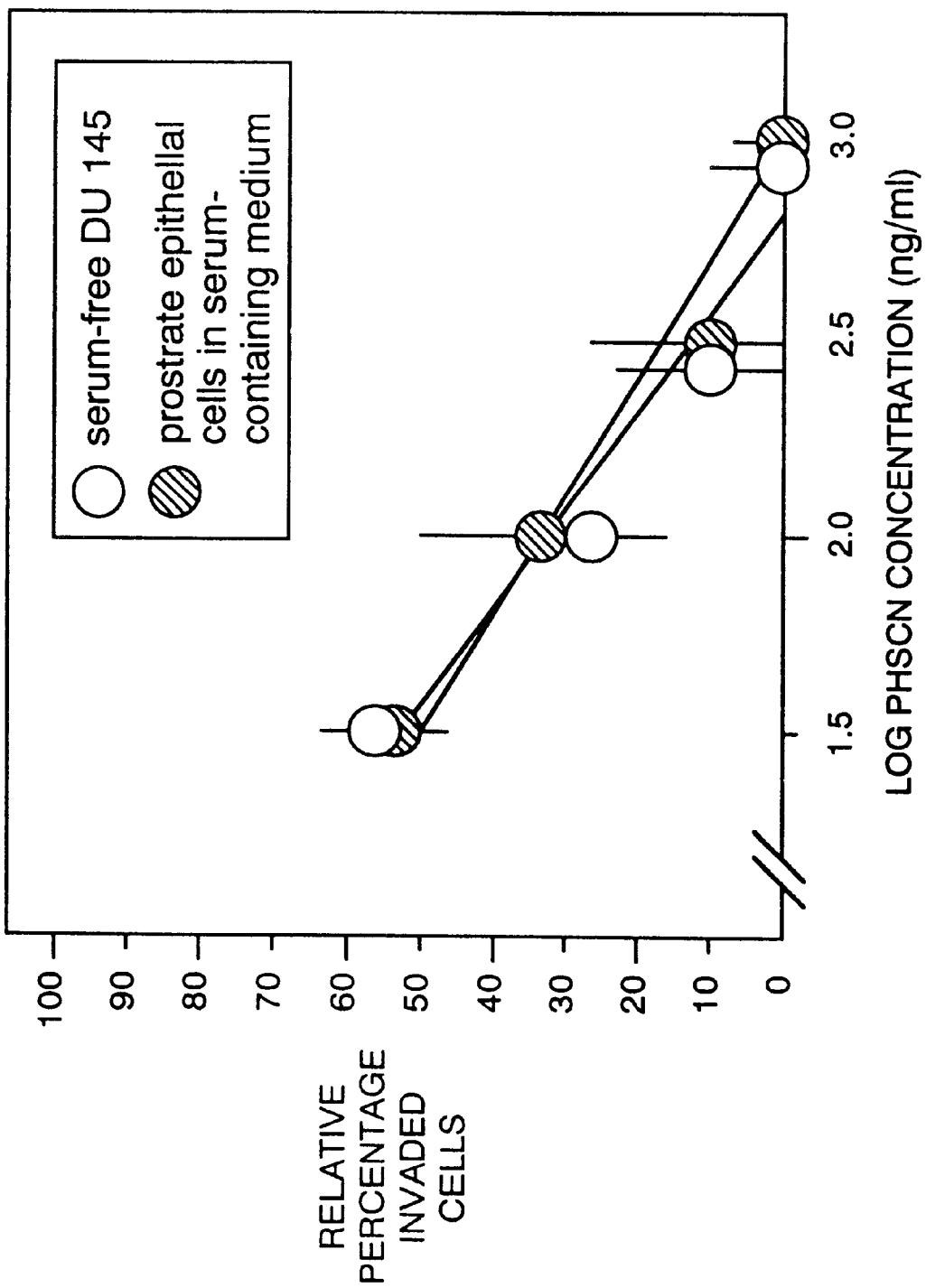
FIG. 6B is a graph showing the results of inhibiting PHSRN (SEQ ID NO:1)-induced invasion by both human prostate cancer cells and normal prostate epithelial cells of the SU-ECM substrate with varying concentrations of the PHSCN SEQ ID NO:86 peptide.

The results of adding varying concentrations of the PHSCN SEQ ID NO:86 peptide to PHSRN (SEQ ID NO:1)-induced invasion of both metastatic DU-145 prostate cancer cells (in serum-free media) and normal human prostate epithelial cells (in 10% fcs), are presented in FIG. 6B. All invasion assays were carried out in 100 ng per ml of the PHSRN SEQ ID NO:1 peptide to induce invasion. Again, the results show that the PHSCN SEQ ID NO:86 peptide exhibits a substantial inhibitory affect on both cell lines at low concentrations, and almost complete inhibition at higher concentrations.

This example demonstrates the PHSCN SEQ ID NO:86 peptide is an effective inhibitor of human prostate cancer cell invasion. In this manner, the PHSCN SEQ ID NO:86 peptide may provide an effective therapy for human prostate cancer by preventing the lethal affects of tumor cell metastasis.

EXAMPLE 10

Inhibiting Invasion Of Rat Prostate Cancer Cells

In this example, the role of the PHSCN SEQ ID NO:86 peptide in inhibiting the invasive behavior of rat metastatic prostate carcinoma MatLyLu (MLL) cells is demonstrated (see Example 4 for the general procedure employed). The result of adding 1 microgram per ml of the PHSCN SEQ ID NO:86 peptide to scrum-induced MLL cells causes complete inhibition of invasion (see FIG. 7A).

The result of adding a varying concentration of the PHSCN SEQ ID NO:86 peptide to PHSRN (SEQ ID NO:1)-induced MLL cells in serum free media is shown in FIG. 7B, where 100 ng per ml of PHSRN SEQ ID NO:1 was used to induce invasion. FIG. 7B indicates that the PHSCN SEQ ID NO:86 peptide exhibits a substantial inhibitory affect even at low concentrations, and almost complete inhibition at higher concentrations. This example demonstrates invasion of rat prostate cancer cells is inhibited in the same manner as human breast cancer cells (see Example 8) and human prostate cancer cells (see Example 9).

EXAMPLE 11

Inhibiting Invasion Of Rat Prostate Cancer Cells

Figure 8:
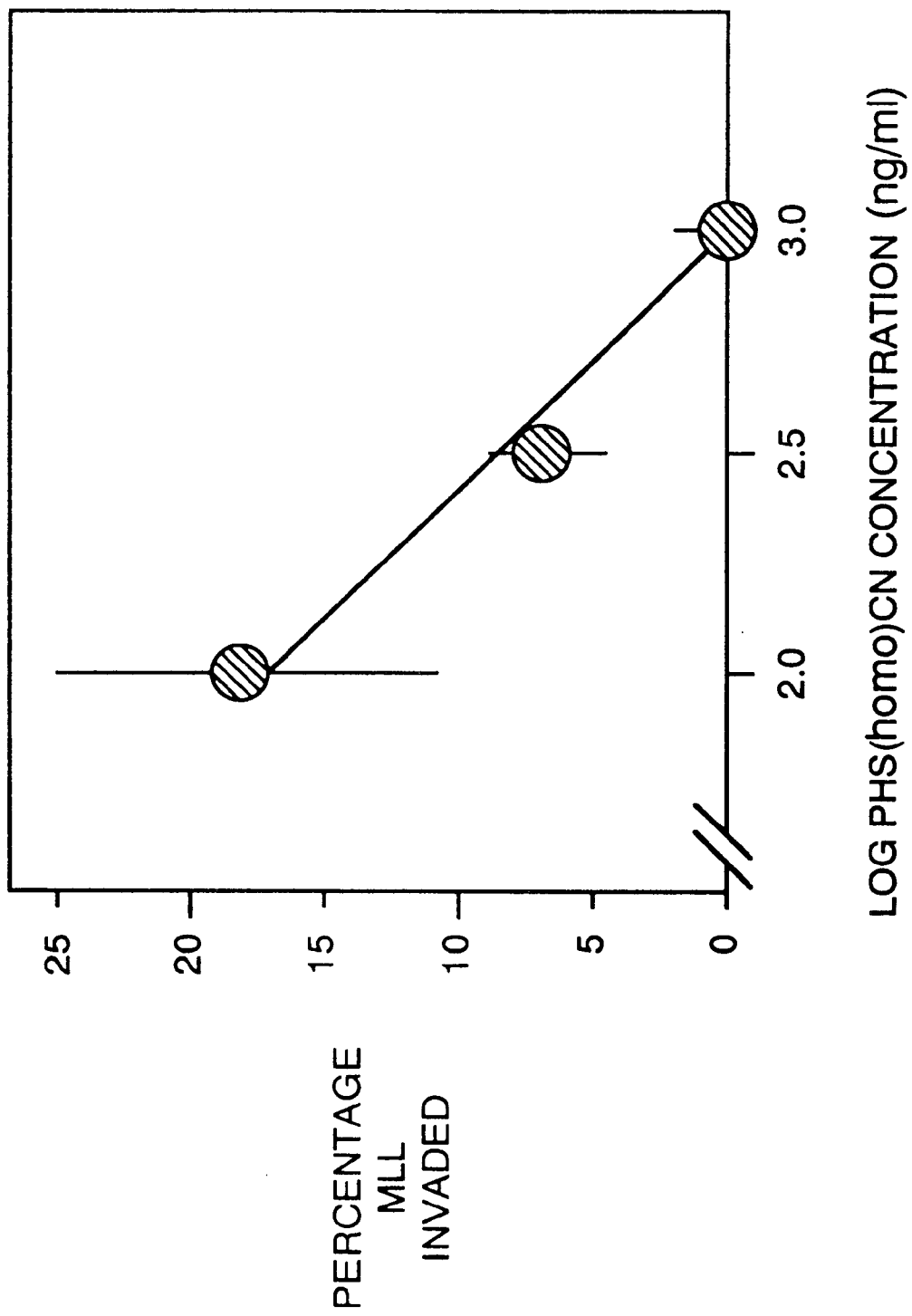
FIG. 8 is a graph showing the results of inhibiting serum-induced rat prostate cancer cell invasion of the SU-ECM substrate with varying concentrations of the PHS (homo)CN SEQ ID NO:85 peptide.

In this example, the role of a homo-cysteine containing peptide (i.e., PHS(hC)N SEQ ID NO:85) in inhibiting the invasive behavior of rat metastatic prostate carcinoma MatLyLu (MLL) cells is demonstrated. The procedure described in Example 10, was employed using SU-ECM substrates in 10% FCS and PHS(hC)N SEQ ID NO:85 instead of PHSCN SEQ ID NO:86. The result of adding varying concentrations of the PHS(hC)N SEQ ID NO:85 peptide to serum-induced MLL cells indicates this peptide also has an inhibitory affect on cell invasion (see FIG. 8). As with the PHSCN SEQ ID NO:86 peptide, the PHS(hC)N SEQ ID NO:85 peptide substantially inhibits invasion at lower concentrations, and completely inhibits invasion at higher concentrations. This example demonstrates that the PHS(hC)N SEQ ID NO:85 peptide has a similar inhibitory affect as the PHSCN SEQ ID NO:86 peptide.

EXAMPLE 12

Inhibiting Growth And Metastasis Of Prostate Cancer Tumors In Vivo

Figure 9A:
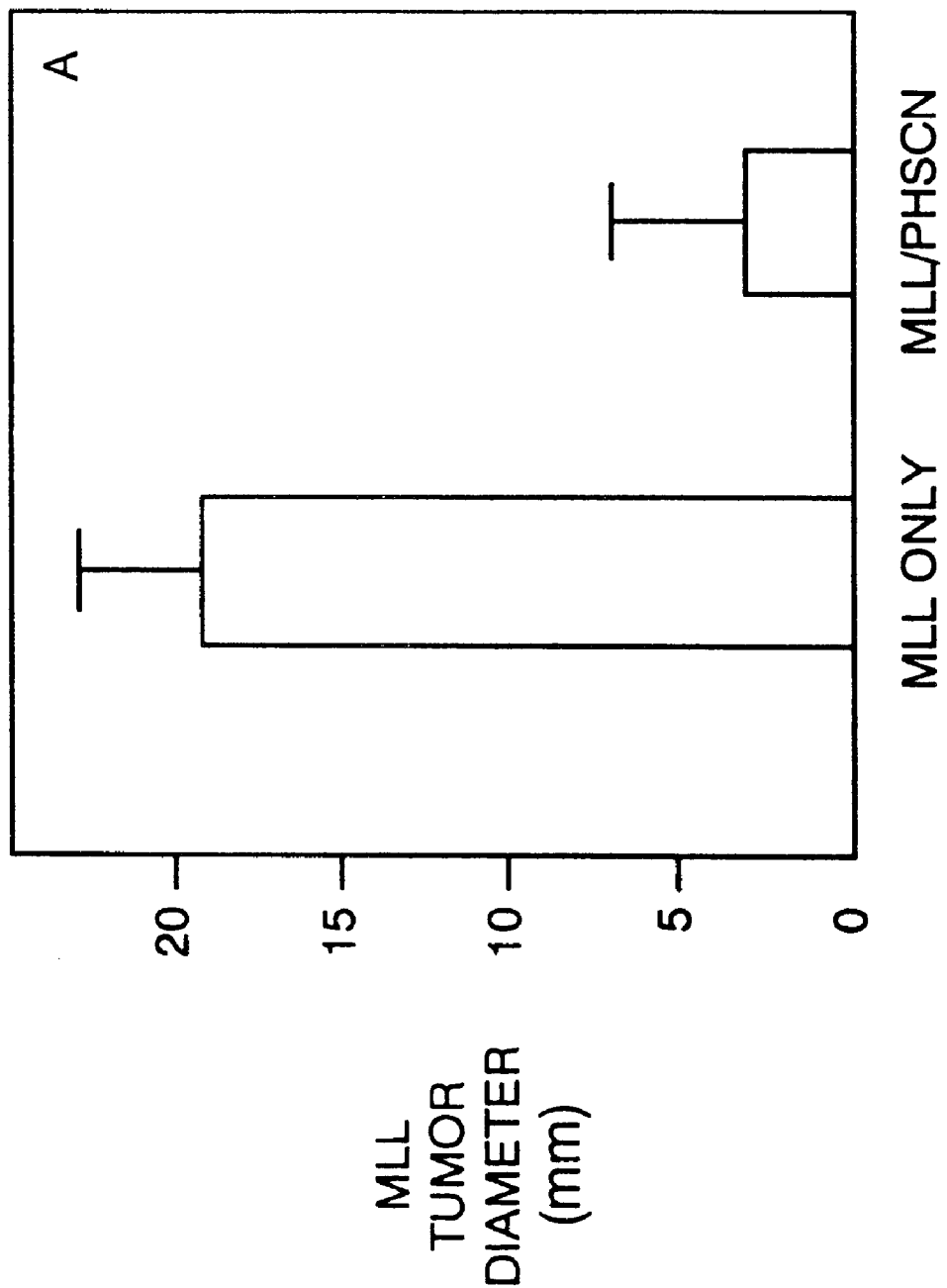
FIG. 9A is a graph showing the results of testing tumor growth in rats injected with prostate cancer cells, with half of the rats receiving treatment with the PHSCN SEQ ID NO:86 peptide, initiated in conjunction with the initial injection.

In this example, the role of the PHSCN SEQ ID NO:86 peptide in inhibiting the growth and metastasis of prostate cancer tumors in vivo is demonstrated. In the first part of this example, four Copenhagen rats were injected with 500,000 MatLyLu (MLL) cells subcutaneously in the thigh. Two of these rats also received 1 mg of the PHSCN SEQ ID NO:86 peptide along with the injected MLL cells, and thereafter received 1 mg of the PHSCN SEQ ID NO:86 peptide injected in their tail vein three time per week for two weeks. The other two injected rats were left untreated. Tumor sizes were measured with calipers on day 14, and the tumors in the untreated rats were removed. The results depicted in FIG. 9A, clearly demonstrate that the PHSCN SEQ ID NO:86 peptide significantly slows the growth of injected MLL tumors in rats. It is possible that the ability of the PHSCN SEQ ID NO:86 peptide to slow tumor growth is due to its inhibition of tumor invasion by normal endothelial cells, an anti-angiogenic effect.

Figure 9B:
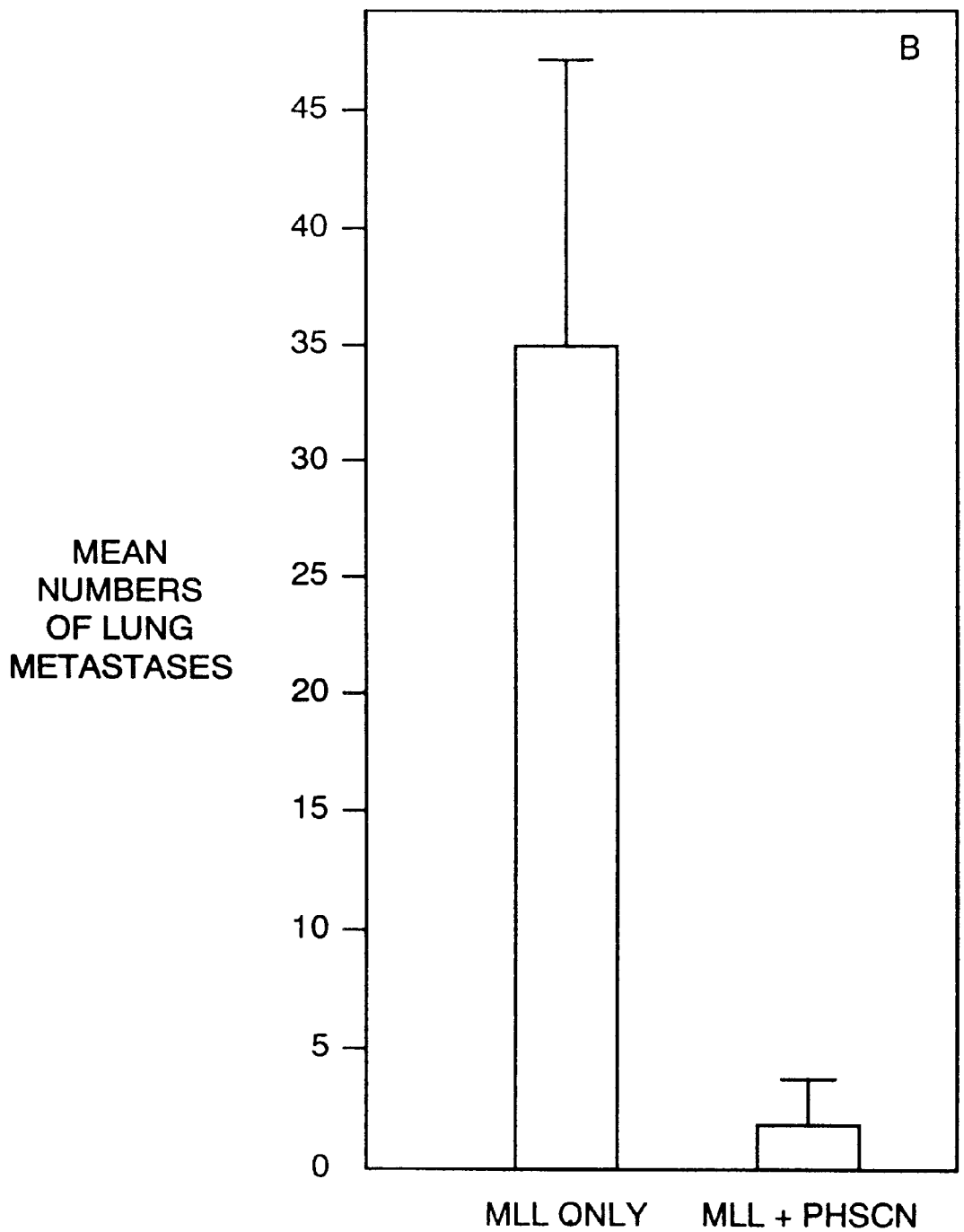

Two weeks after the size of the tumors were measured, the rats were sacrificed and the mean number of lung metastases was determined at 10-fold magnification. The mean number of lung metastases in the untreated mice (MLL only) was nearly 35 in spite of the fact that the initial prostate tumors had been removed when their size was measured. The mean number of lung metastases in the treated mice (MLL+ PHSCN SEQ ID NO:86) was less than 5, even though the initial prostate tumors were never removed because they were too small. This striking difference in mean number of metastases, depicted in FIG. 9B, indicates that the PHSCN SEQ ID NO:86 peptide significantly inhibits tumor cell metastasis in rats. In this manner, the PHSCN SEQ ID NO:86 peptide provides effective in vivo therapy for cancer by preventing the lethal effects of tumor cell growth and metastasis.

EXAMPLE 13

Inhibiting Growth And Metastasis Of Prostate Cancer In Vivo

Figure 10A:
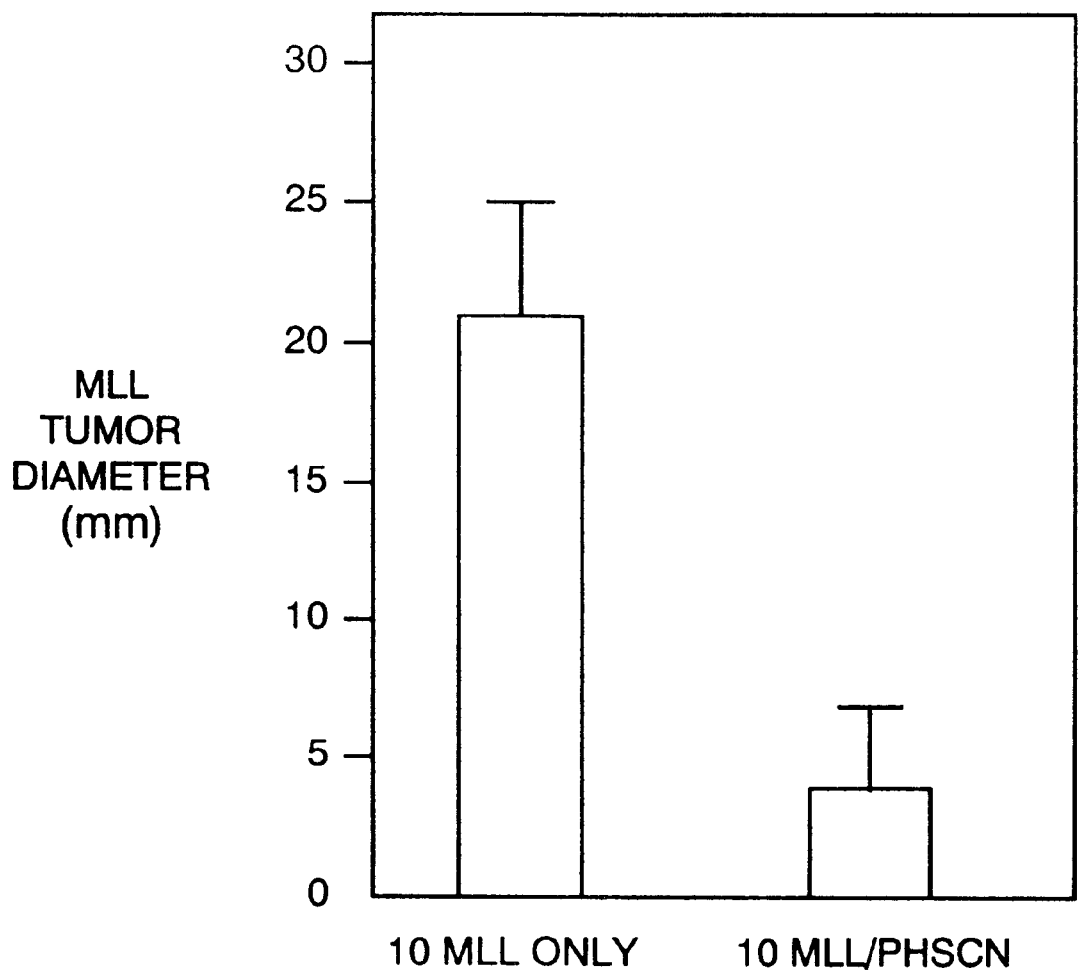
FIG. 10A is a graph showing the results of testing tumor growth in rats injected with prostate cancer cells, with half of the rats receiving treatment with the PHSCN SEQ ID NO:86 peptide, initiated 24 hours after the initial cancer cell injection.

In this example, as in Example 12, the role of the PHSCN SEQ ID NO:86 peptide in inhibiting the growth and metastasis of prostate cancer tumors in vivo is demonstrated. In the first part of this example, 20 Copenhagen rats were injected with 500,000 MatLyuLu (MLL) cells subcutaneously in the thigh. To more closely approximate a real clinical situation, PHSCN SEQ ID NO:86 peptide treatment of 10 of these rats was initiated after 24 hours, instead of immediately. The 10 treated rats (MLL/PHSCN SEQ ID NO:86) received a total of 5 i.v. injections of 1 mg of the PHSCN SEQ ID NO:86 peptide through the tail vein over two weeks. Tumor sizes were measured with calipers on day 14, and the tumors in the untreated rats were removed. Since the injected tumors in the MLL/PHSCN SEQ ID NO:86 rats were still small, they were retained in the rats for another 7 to 9 days following the last PHSCN SEQ ID NO:86 injection. At this time, their sizes were all greater than 2 cm, and they were also removed. The result of the first part of this example, depicted in FIG. 10A, clearly indicates that the PHSCN SEQ ID NO:86 peptide, even when administered after the tumor cells have "seeded", substantially slows the growth of rat prostate cancer tumors.

The dramatic growth-inhibitory effect of the PHSCN SEQ ID NO:86 peptide on MLL tumors may be due to their inhibition of the invasion of host endothelial cells into the tumor. Host endothelial cell invasion may be induced by the secretion of large amounts of proteinases from the tumors, and the resulting fragmentation of host plasma fibronectin. Fibronectin fragments have been shown to stimulate the migratory/invasive behaviors of normal mesenchymal and endothelial cells. This angiogenic process is believed to occur during normal wound healing. Thus, the ability of metastatic cells to be constitutively induced by intact plasma fibronectin to express proteinases and invade may play a central role both in tumor cell invasion and in tumor growth. In this manner, the PHSCN SEQ ID NO:86 peptide is an effective chemotherapeutic to prevent the growth of tumors in vivo.

Figure 10C:
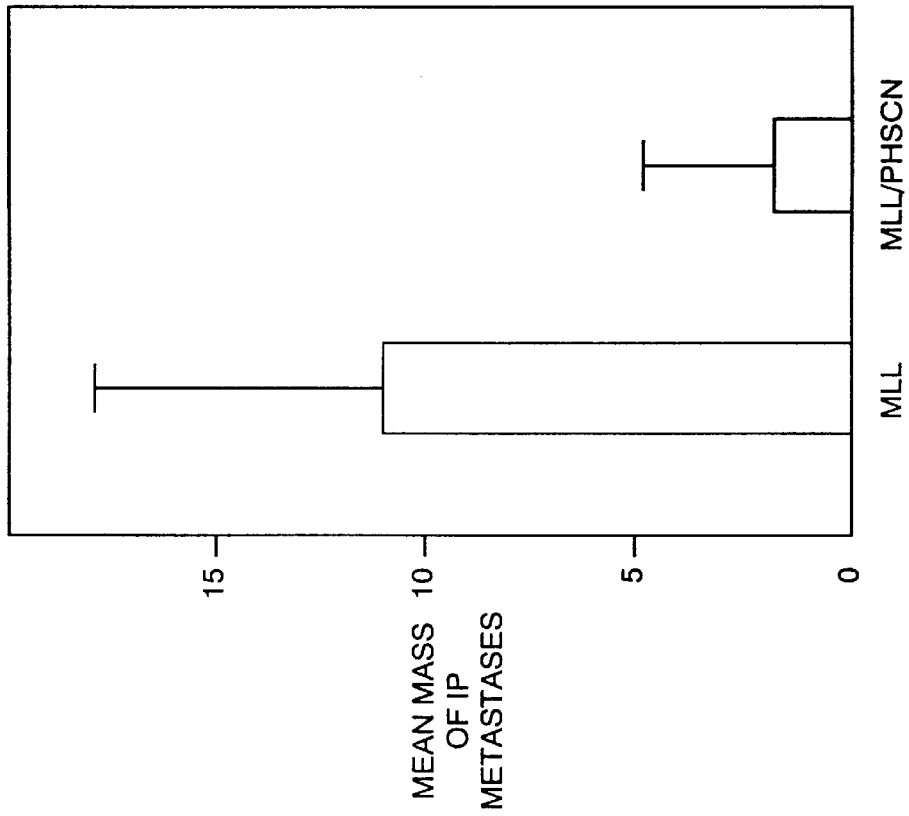
Figure 10B:
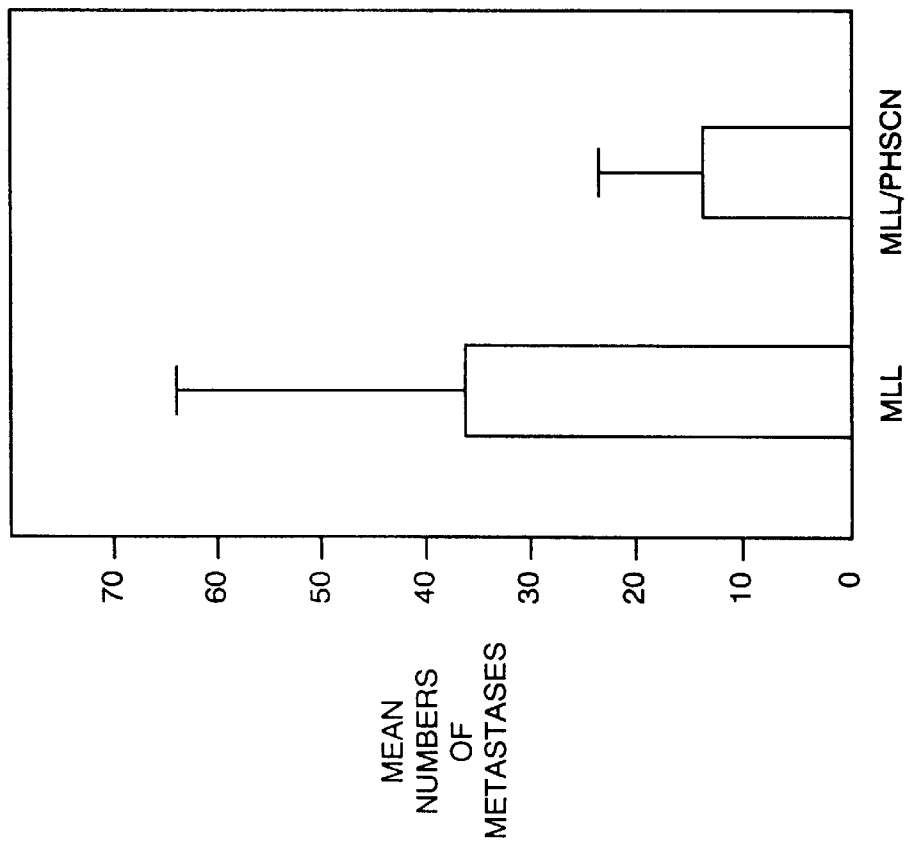

In the second part of this example, the MLL/PHSCN SEQ ID NO:86 rats received 2 more i.v. doses of the PHSCN SEQ ID NO:86 peptide prior to sacrifice. Ten days after the sizes of the injected primary tumors were determined, all the rats in the two groups (MLL only and MLL/PHSCN SEQ ID NO:86) were sacrificed, and the number of lung metastases was determined at 7.5-fold magnification. As can be seen in FIG. 10B, there is a significant reduction in the mean numbers of lung metastases in the rats which received PHSCN SEQ ID NO:86 treatment as compared to the untreated rats.

The 20 rats described in parts one and two of this example were also examined for metastatic tissues in their lymphatic systems. All of these metastases were dissected and weighed. FIG. 10C plots the mean masses of intraperitoneal metastases (grams) for the two groups of 10 rats. As is clearly demonstrated, there is a significant reduction in the mean masses of lymphatic metastases in the rats which received PHSCN SEQ ID NO:86 peptide treatment, as compared to the untreated rats. This may be due to the anti-angiogenic effect of the PHSCN SEQ ID NO:86 peptide, as described in part one of this example. In this manner, the PHSCN SEQ ID NO:86 peptide maybe an effective anti-metastatic, growth-inhibiting chemotherapeutic agent for use in the treatment of cancer.

From the above, it should be clear that the present invention provides an anticancer approach that is reliable for a wide variety of tumor types, and particularly suitable for invasive tumors. Importantly, the treatment is effective with minimal host toxicity.

SEQUENCE LISTING (1) GENERAL INFORMATION:

(iii) NUMBER OF SEQUENCES: 106

(2) INFORMATION FOR SEQ ID NO:1:

(i) SEQUENCE CHARACTERISTICS:
      (A) LENGTH: 5 amino acids
      (B) TYPE: amino acid
      (C) STRANDEDNESS: Not Relevant
      (D) TOPOLOGY: Not Relevant (ii) MOLECULE TYPE: peptide (xi) SEQUENCE DESCRIPTION: SEQ ID NO:1:

Pro His Ser Arg Asn
1             5

(2) INFORMATION FOR SEQ ID NO:2:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:2:

Ile Lys Val Ala Val
1          5

(2) INFORMATION FOR SEQ ID NO:3:

(i) SEQUENCE CHARACTERISTICS:
        (A) LENGTH: 6 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:3:

Pro His Ser Arg Asn Ser
1          5

(2) INFORMATION FOR SEQ ID NO:4:

(i) SEQUENCE CHARACTERISTICS:
        (A) LENGTH: 7 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:4:

Pro His Ser Arg Asn Ser Ile
1          5

(2) INFORMATION FOR SEQ ID NO:5:

(i) SEQUENCE CHARACTERISTICS:
        (A) LENGTH: 8 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:5:

Pro His Ser Arg Asn Ser Ile Thr
1          5

(2) INFORMATION FOR SEQ ID NO:6:

(i) SEQUENCE CHARACTERISTICS:
        (A) LENGTH: 9 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:6:

Pro His Ser Arg Asn Ser Ile Thr Leu
1          5

(2) INFORMATION FOR SEQ ID NO:7:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:7:

```
Pro His Ser Arg Asn Ser Ile Thr Leu Thr
1               5                   10
```

(2) INFORMATION FOR SEQ ID NO:8:

(i) SEQUENCE CHARACTERISTICS:
        (A) LENGTH: 11 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:8:

```
Pro His Ser Arg Asn Ser Ile Thr Leu Thr Asn
1               5                   10
```

(2) INFORMATION FOR SEQ ID NO:9:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:9:

```
Pro His Ser Arg Asn Ser Ile Thr Leu Thr Asn Leu
1               5                   10
```

(2) INFORMATION FOR SEQ ID NO:10:

(i) SEQUENCE CHARACTERISTICS:
        (A) LENGTH: 13 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:10:

```
Pro His Ser Arg Asn Ser Ile Thr Leu Thr Asn Leu Thr
1               5                   10
```

(2) INFORMATION FOR SEQ ID NO:11:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:11:

```
Pro His Ser Arg Asn Ser Ile Thr Leu Thr Asn Leu Thr Pro
1               5                   10
```

(2) INFORMATION FOR SEQ ID NO:12:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:12:

```
Pro His Ser Arg Asn Ser Ile Thr Leu Thr Asn Leu Thr Pro Gly
1               5                  10                  15
```

(2) INFORMATION FOR SEQ ID NO:13:

(i) SEQUENCE CHARACTERISTICS:
        (A) LENGTH: 18 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:13:

```
Pro Glu His Phe Ser Gly Arg Pro Arg Glu Asp Arg Val Pro His Ser
1               5                  10                  15
Arg Asn
```

(2) INFORMATION FOR SEQ ID NO:14:

(i) SEQUENCE CHARACTERISTICS:
        (A) LENGTH: 17 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:14:

```
Glu His Phe Ser Gly Arg Pro Arg Glu Asp Arg Val Pro His Ser Arg
1               5                  10                  15
Asn
```

(2) INFORMATION FOR SEQ ID NO:15:

(i) SEQUENCE CHARACTERISTICS:
        (A) LENGTH: 16 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:15:

```
His Phe Ser Gly Arg Pro Arg Glu Asp Arg Val Pro His Ser Arg Asn
1               5                  10                  15
```

(2) INFORMATION FOR SEQ ID NO:16:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: Not Relevant (ii) MOLECULE TYPE: peptide

```
        (xi) SEQUENCE DESCRIPTION: SEQ ID NO:16:

Phe Ser Gly Arg Pro Arg Glu Asp Arg Val Pro His Ser Arg Asn
 1               5                  10                  15

(2) INFORMATION FOR SEQ ID NO:17:

(i) SEQUENCE CHARACTERISTICS:
            (A) LENGTH: 14 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:17:

Ser Gly Arg Pro Arg Glu Asp Arg Val Pro His Ser Arg Asn
 1               5                  10

(2) INFORMATION FOR SEQ ID NO:18:

(i) SEQUENCE CHARACTERISTICS:
            (A) LENGTH: 13 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:18:

Gly Arg Pro Arg Glu Asp Arg Val Pro His Ser Arg Asn
 1               5                  10

(2) INFORMATION FOR SEQ ID NO:19:

(i) SEQUENCE CHARACTERISTICS:
            (A) LENGTH: 12 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:19:

Arg Pro Arg Glu Asp Arg Val Pro His Ser Arg Asn
 1               5                  10

(2) INFORMATION FOR SEQ ID NO:20:

(i) SEQUENCE CHARACTERISTICS:
            (A) LENGTH: 11 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:20:

Pro Arg Glu Asp Arg Val Pro His Ser Arg Asn
 1               5                  10

(2) INFORMATION FOR SEQ ID NO:21:

(i) SEQUENCE CHARACTERISTICS:
            (A) LENGTH: 10 amino acids
            (B) TYPE: amino acid
            (C) STRANDEDNESS: Not Relevant
            (D) TOPOLOGY: Not Relevant (ii) MOLECULE TYPE: peptide
```

(xi) SEQUENCE DESCRIPTION: SEQ ID NO:21:

Arg Glu Asp Arg Val Pro His Ser Arg Asn
1               5                   10

(2) INFORMATION FOR SEQ ID NO:22:

(i) SEQUENCE CHARACTERISTICS:
            (A) LENGTH: 9 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:22:

Glu Asp Arg Val Pro His Ser Arg Asn
1               5

(2) INFORMATION FOR SEQ ID NO:23:

(i) SEQUENCE CHARACTERISTICS:
            (A) LENGTH: 8 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:23:

Asp Arg Val Pro His Ser Arg Asn
1               5

(2) INFORMATION FOR SEQ ID NO:24:

(i) SEQUENCE CHARACTERISTICS:
            (A) LENGTH: 7 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:24:

Arg Val Pro His Ser Arg Asn
1               5

(2) INFORMATION FOR SEQ ID NO:25:

(i) SEQUENCE CHARACTERISTICS:
            (A) LENGTH: 6 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:25:

Val Pro His Ser Arg Asn
1               5

(2) INFORMATION FOR SEQ ID NO:26:

(i) SEQUENCE CHARACTERISTICS:
            (A) LENGTH: 28 amino acids
            (B) TYPE: amino acid
            (C) STRANDEDNESS: Not Relevant
            (D) TOPOLOGY: Not Relevant (ii) MOLECULE TYPE: peptide -continued (xi) SEQUENCE DESCRIPTION: SEQ ID NO:26:

Pro Glu His Phe Ser Gly Arg Pro Arg Glu Asp Arg Val Pro His Ser
1               5                   10                  15

Arg Asn Ser Ile Thr Leu Thr Asn Leu Thr Pro Gly
            20                  25

(2) INFORMATION FOR SEQ ID NO:27:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:27:

Pro Pro Ser Arg Asn
1           5

(2) INFORMATION FOR SEQ ID NO:28:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:28:

His His Ser Arg Asn
1           5

(2) INFORMATION FOR SEQ ID NO:29:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:29:

His Pro Ser Arg Asn
1           5

(2) INFORMATION FOR SEQ ID NO:30:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:30:

Pro His Thr Arg Asn
1           5

(2) INFORMATION FOR SEQ ID NO:31:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:31:

His His Thr Arg Asn
1               5

(2) INFORMATION FOR SEQ ID NO:32:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:32:

His Pro Thr Arg Asn
1               5

(2) INFORMATION FOR SEQ ID NO:33:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:33:

Pro His Ser Asn Asn
1               5

(2) INFORMATION FOR SEQ ID NO:34:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:34:

His His Ser Asn Asn
1               5

(2) INFORMATION FOR SEQ ID NO:35:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:35:

His Pro Ser Asn Asn
1               5

(2) INFORMATION FOR SEQ ID NO:36:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:36:

Pro His Thr Asn Asn
1               5

(2) INFORMATION FOR SEQ ID NO:37:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:37:

His His Thr Asn Asn
1               5

(2) INFORMATION FOR SEQ ID NO:38:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:38:

His Pro Thr Asn Asn
1               5

(2) INFORMATION FOR SEQ ID NO:39:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:39:

Pro His Ser Lys Asn
1               5

(2) INFORMATION FOR SEQ ID NO:40:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:40:

His His Ser Lys Asn
1               5

(2) INFORMATION FOR SEQ ID NO:41:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:41:

His Pro Ser Lys Asn
1               5

(2) INFORMATION FOR SEQ ID NO:42:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:42:

Pro His Thr Lys Asn
1               5

(2) INFORMATION FOR SEQ ID NO:43:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:43:

His His Thr Lys Asn
1               5

(2) INFORMATION FOR SEQ ID NO:44:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:44:

His Pro Thr Lys Asn
1               5

(2) INFORMATION FOR SEQ ID NO:45:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:45:

Pro His Ser Arg Arg
1               5

(2) INFORMATION FOR SEQ ID NO:46:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:46:

His His Ser Arg Arg
1               5

(2) INFORMATION FOR SEQ ID NO:47:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:47:

His Pro Ser Arg Arg
1               5

(2) INFORMATION FOR SEQ ID NO:48:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:48:

Pro His Thr Arg Arg
1               5

(2) INFORMATION FOR SEQ ID NO:49:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:49:

His His Thr Arg Arg
1               5

(2) INFORMATION FOR SEQ ID NO:50:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:50:

His Pro Thr Arg Arg
1               5

(2) INFORMATION FOR SEQ ID NO:51:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:51:

Pro His Ser Asn Arg
1               5

(2) INFORMATION FOR SEQ ID NO:52:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:52:

His His Ser Asn Arg
1               5

(2) INFORMATION FOR SEQ ID NO:53:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:53:

His Pro Ser Asn Arg
1               5

(2) INFORMATION FOR SEQ ID NO:54:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:54:

Pro His Thr Asn Arg
1               5

(2) INFORMATION FOR SEQ ID NO:55:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:55:

His His Thr Asn Arg
1               5

(2) INFORMATION FOR SEQ ID NO:56:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:56:

His Pro Thr Asn Arg
1               5

(2) INFORMATION FOR SEQ ID NO:57:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:57:

Pro His Ser Lys Arg
1               5

(2) INFORMATION FOR SEQ ID NO:58:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:58:

His His Ser Lys Arg
1               5

(2) INFORMATION FOR SEQ ID NO:59:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:59:

His Pro Ser Lys Arg
1               5

(2) INFORMATION FOR SEQ ID NO:60:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:60:

Pro His Thr Lys Arg
1               5

(2) INFORMATION FOR SEQ ID NO:61:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:61:

His His Thr Lys Arg
1               5

(2) INFORMATION FOR SEQ ID NO:62:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:62:

His Pro Thr Lys Arg
1               5

(2) INFORMATION FOR SEQ ID NO:63:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:63:

Pro His Ser Arg Lys
1               5

(2) INFORMATION FOR SEQ ID NO:64:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:64:

His His Ser Arg Lys
1               5

(2) INFORMATION FOR SEQ ID NO:65:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:65:

His Pro Ser Arg Lys
1               5

(2) INFORMATION FOR SEQ ID NO:66:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:66:

Pro His Thr Arg Lys
1               5

(2) INFORMATION FOR SEQ ID NO:67:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:67:

His His Thr Arg Lys
1               5

(2) INFORMATION FOR SEQ ID NO:68:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:68:

His Pro Thr Arg Lys
1               5

(2) INFORMATION FOR SEQ ID NO:69:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:69:

Pro His Ser Asn Lys
1               5

(2) INFORMATION FOR SEQ ID NO:70:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:70:

His His Ser Asn Lys
1               5

(2) INFORMATION FOR SEQ ID NO:71:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:71:

His Pro Ser Asn Lys
1               5

(2) INFORMATION FOR SEQ ID NO:72:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:72:

Pro His Thr Asn Lys
1               5

(2) INFORMATION FOR SEQ ID NO:73:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:73:

His His Thr Asn Lys
1               5

(2) INFORMATION FOR SEQ ID NO:74:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:74:

His Pro Thr Asn Lys
1               5

(2) INFORMATION FOR SEQ ID NO:75:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:75:

Pro His Ser Lys Lys
1               5

(2) INFORMATION FOR SEQ ID NO:76:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:76:

His His Ser Lys Lys
1               5

(2) INFORMATION FOR SEQ ID NO:77:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:77:

His Pro Ser Lys Lys
1               5

(2) INFORMATION FOR SEQ ID NO:78:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:78:

Pro His Thr Lys Lys
1               5

(2) INFORMATION FOR SEQ ID NO:79:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:79:

His His Thr Lys Lys
1               5

(2) INFORMATION FOR SEQ ID NO:80:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:80:

His Pro Thr Lys Lys
1               5

(2) INFORMATION FOR SEQ ID NO:81:

(i) SEQUENCE CHARACTERISTICS:
        (A) LENGTH: 3 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:81:

Arg Gly Asp
1

(2) INFORMATION FOR SEQ ID NO:82:

(i) SEQUENCE CHARACTERISTICS:
            (A) LENGTH: 6 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:82:

Pro His Ser Arg Asn Cys
1               5

(2) INFORMATION FOR SEQ ID NO:83:

(i) SEQUENCE CHARACTERISTICS:
            (A) LENGTH: 6 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:83:

Gly Arg Gly Asp Ser Pro
1               5

(2) INFORMATION FOR SEQ ID NO:84:

(i) SEQUENCE CHARACTERISTICS:
            (A) LENGTH: 6 amino acids
            (B) TYPE: amino acid
            (C) STRANDEDNESS: Not Relevant
            (D) TOPOLOGY: Not Relevant (ii) MOLECULE TYPE: peptide (ix) FEATURE:
            (A) NAME/KEY: Modified-site
            (B) LOCATION: 1
            (D) OTHER INFORMATION: /note= "This X is a placeholder for
                N-terminal acetylation."

(ix) FEATURE:
            (A) NAME/KEY: Modified-site
            (B) LOCATION: 9
            (D) OTHER INFORMATION: /note= "X represents an amino
                group."

(ix) FEATURE:
            (A) NAME/KEY: Modified-site
            (B) LOCATION: 2
            (D) OTHER INFORMATION: /note= "The number of amino acids
                at this position may vary from between 0 and 100, or
                more."

(ix) FEATURE:
            (A) NAME/KEY: Modified-site
            (B) LOCATION: 8
            (D) OTHER INFORMATION: /note= "The number of amino acids
                at this position may vary from between 0 and 100, or
                more."

(xi) SEQUENCE DESCRIPTION: SEQ ID NO:84:

```
Gly Arg Gly Glu Ser Pro
1               5

(2) INFORMATION FOR SEQ ID NO:85:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Modified-site
        (B) LOCATION: 4
        (D) OTHER INFORMATION: /note= "The residue in this
            position is a homo-cysteine containing peptide."

(xi) SEQUENCE DESCRIPTION: SEQ ID NO:85:

Pro His Ser Cys Asn
1               5

(2) INFORMATION FOR SEQ ID NO:86:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:86:

Pro His Ser Cys Asn
1               5

(2) INFORMATION FOR SEQ ID NO:87:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:87:

Cys His Ser Arg Asn
1               5

(2) INFORMATION FOR SEQ ID NO:88:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:88:

Pro Cys Ser Arg Asn
1               5

(2) INFORMATION FOR SEQ ID NO:89:

(i) SEQUENCE CHARACTERISTICS:
        (A) LENGTH: 5 amino acids
        (B) TYPE: amino acid
        (C) STRANDEDNESS: Not Relevant
```

(D) TOPOLOGY: Not Relevant (ii) MOLECULE TYPE: peptide (xi) SEQUENCE DESCRIPTION: SEQ ID NO:89:

Pro His Cys Arg Asn
1               5

(2) INFORMATION FOR SEQ ID NO:90:

(i) SEQUENCE CHARACTERISTICS:
           (A) LENGTH: 5 amino acids
           (B) TYPE: amino acid
           (C) STRANDEDNESS: Not Relevant
           (D) TOPOLOGY: Not Relevant (ii) MOLECULE TYPE: peptide (xi) SEQUENCE DESCRIPTION: SEQ ID NO:90:

Pro His Ser Arg Cys
1               5

(2) INFORMATION FOR SEQ ID NO:91:

(i) SEQUENCE CHARACTERISTICS:
           (A) LENGTH: 5 amino acids
           (B) TYPE: amino acid
           (C) STRANDEDNESS: Not Relevant
           (D) TOPOLOGY: Not Relevant (ii) MOLECULE TYPE: peptide (ix) FEATURE:
           (A) NAME/KEY: Modified-site
           (B) LOCATION: 4
           (D) OTHER INFORMATION: /note= "The amino acid in this
                position is selected from the group consisting of
                homo-cysteine, the D-isomer of cysteine, histidine, or
                penicillamine."

(xi) SEQUENCE DESCRIPTION: SEQ ID NO:91:

Pro His Ser Xaa Asn
1               5

(2) INFORMATION FOR SEQ ID NO:92:

(i) SEQUENCE CHARACTERISTICS:
           (A) LENGTH: 5 amino acids
           (B) TYPE: amino acid
           (C) STRANDEDNESS: Not Relevant
           (D) TOPOLOGY: Not Relevant (ii) MOLECULE TYPE: peptide (ix) FEATURE:
           (A) NAME/KEY: Modified-site
           (B) LOCATION: 1
           (D) OTHER INFORMATION: /note= "The residue in this
                position is either proline, histidine, or not an amino
                acid."

(ix) FEATURE:
           (A) NAME/KEY: Modified-site
           (B) LOCATION: 4
           (D) OTHER INFORMATION: /note= "The residue in this
                position is an amino acid selected from the group
                consisting of the L-isomer of cysteine, the D-isomer of
                cysteine, homo-cysteine, histidine, or pencillamine."

(xi) SEQUENCE DESCRIPTION: SEQ ID NO:92:

Xaa His Ser Xaa Asn
1               5

(2) INFORMATION FOR SEQ ID NO:93:

(i) SEQUENCE CHARACTERISTICS:
       (A) LENGTH: 5 amino acids
       (B) TYPE: amino acid
       (C) STRANDEDNESS: Not Relevant
       (D) TOPOLOGY: Not Relevant (ii) MOLECULE TYPE: peptide (ix) FEATURE:
       (A) NAME/KEY: Modified-site
       (B) LOCATION: 1
       (D) OTHER INFORMATION: /note= "The residue at this
           position is an amino acid selected from the group
           consisting of proline, glycine, valine, histidine,
           isoleucine, phenylalanine, tyrosine, and tryptophan."

(ix) FEATURE:
       (A) NAME/KEY: Modified-site
       (B) LOCATION: 2
       (D) OTHER INFORMATION: /note= "The residue at this
           position is an amino acid selected fromthe group
           consisting of histidine, proline, tyrosine, asparagine,
           glutamine, arginine, lysine, phenylalanine, and
           tryptophan."

(ix) FEATURE:
       (A) NAME/KEY: Modified-site
       (B) LOCATION: 3
       (D) OTHER INFORMATION: /note= "The residue at this
           position is an amino acid selected from the group
           consisting of serine, threonine, alanine, tyrosine,
           leucine, histidine, asparagine, and glutamine."

(ix) FEATURE:
       (A) NAME/KEY: Modified-site
       (B) LOCATION: 4
       (D) OTHER INFORMATION: /note= "The residue at this
           position is an amino acid selected from the group
           consisting of cysteine, homo-cysteine, penicillamine,
           histidine, tyrosine, asparagine, glutamine, and
           methionine."

(ix) FEATURE:
       (A) NAME/KEY: Modified-site
       (B) LOCATION: 5
       (D) OTHER INFORMATION: /note= "The residue at this
           position is an amino acid selected from the group
           consisting of asparagine, glutamine, serine, threonine,
           histidine, and tyrosine."

(xi) SEQUENCE DESCRIPTION: SEQ ID NO:93:

Xaa Xaa Xaa Xaa Xaa
1               5

(2) INFORMATION FOR SEQ ID NO:94:

(i) SEQUENCE CHARACTERISTICS:
       (A) LENGTH: 5 amino acids
       (B) TYPE: amino acid
       (C) STRANDEDNESS: Not Relevant
       (D) TOPOLOGY: Not Relevant (ii) MOLECULE TYPE: peptide (xi) SEQUENCE DESCRIPTION: SEQ ID NO:94:

Ile Cys Val Ala Val
1               5

(2) INFORMATION FOR SEQ ID NO:95:

(i) SEQUENCE CHARACTERISTICS:
       (A) LENGTH: 4 amino acids
       (B) TYPE: amino acid

```
            (C) STRANDEDNESS: Not Relevant
            (D) TOPOLOGY: Not Relevant (ii) MOLECULE TYPE: peptide (xi) SEQUENCE DESCRIPTION: SEQ ID NO:95:

His Ser Cys Lys
1

(2) INFORMATION FOR SEQ ID NO:96:

(i) SEQUENCE CHARACTERISTICS:
            (A) LENGTH: 4 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:96:

His Ser Cys Asn
1

(2) INFORMATION FOR SEQ ID NO:97:

(i) SEQUENCE CHARACTERISTICS:
            (A) LENGTH: 4 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:97:

His Ser Cys Arg
1

(2) INFORMATION FOR SEQ ID NO:98:

(i) SEQUENCE CHARACTERISTICS:
            (A) LENGTH: 4 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:98:

His Thr Cys Lys
1

(2) INFORMATION FOR SEQ ID NO:99:

(i) SEQUENCE CHARACTERISTICS:
            (A) LENGTH: 4 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:99:

His Thr Cys Asn
1

(2) INFORMATION FOR SEQ ID NO:100:

(i) SEQUENCE CHARACTERISTICS:
            (A) LENGTH: 4 amino acids
            (B) TYPE: amino acid
```

(C) STRANDEDNESS: Not Relevant
            (D) TOPOLOGY: Not Relevant (ii) MOLECULE TYPE: peptide (xi) SEQUENCE DESCRIPTION: SEQ ID NO:100:

His Thr Cys Arg
1

(2) INFORMATION FOR SEQ ID NO:101:

(i) SEQUENCE CHARACTERISTICS:
            (A) LENGTH: 4 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:101:

Pro Ser Cys Lys
1

(2) INFORMATION FOR SEQ ID NO:102:

(i) SEQUENCE CHARACTERISTICS:
            (A) LENGTH: 4 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:102:

Pro Ser Cys Asn
1

(2) INFORMATION FOR SEQ ID NO:103:

(i) SEQUENCE CHARACTERISTICS:
            (A) LENGTH: 4 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:103:

Pro Ser Cys Arg
1

(2) INFORMATION FOR SEQ ID NO:104:

(i) SEQUENCE CHARACTERISTICS:
            (A) LENGTH: 4 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:104:

Pro Thr Cys Lys
1

(2) INFORMATION FOR SEQ ID NO:105:

(i) SEQUENCE CHARACTERISTICS:
            (A) LENGTH: 4 amino acids
            (B) TYPE: amino acid

```
            (C) STRANDEDNESS: Not Relevant
            (D) TOPOLOGY: Not Relevant (ii) MOLECULE TYPE: peptide (xi) SEQUENCE DESCRIPTION: SEQ ID NO:105:

Pro Thr Cys Asn
 1

(2) INFORMATION FOR SEQ ID NO:106:

(i) SEQUENCE CHARACTERISTICS:
            (A) LENGTH: 4 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:106:

Pro Thr Cys Arg
```

I claim:

1. A peptide consisting of the amino acid sequence PHSCN (SEQ ID NO.:86).

2. A peptide consisting of the amino acid sequence PHSXN (SEQ ID NO.:91), where X is an amino acid selected from the group consisting of homo-cysteine, the D-isomer of cysteine, histidine, or penicillamine.

3. The peptide of claim 2 wherein said peptide's amino terminus is blocked with an acetyl group, and said peptide's carboxyl terminus is blocked with an amide group.

4. A peptide consisting of the amino acid sequence $X_1HSX_2N$ (SEQ ID NO.:92), wherein $X_1$ is either proline, histidine, or not an amino acid, and $X_2$ is an amino acid selected from the group consisting of the L-isomer of cysteine, the D-isomer of cysteine, homo-cysteine, histidine, or penicillamine.

5. The peptide of claim 4, wherein said peptide's amino terminus is blocked with an acetyl group, and said peptide's carboxyl terminus is blocked with an amide group.

* * * * *